United States Patent
Qie et al.

(10) Patent No.: US 9,890,301 B2
(45) Date of Patent: Feb. 13, 2018

(54) WATER-BASED PRESSURE-SENSITIVE ADHESIVE COMPOSITIONS

(71) Applicant: 3M INNOVATIVE PROPERTIES COMPANY, St. Paul, MN (US)

(72) Inventors: Lili Qie, Woodbury, MN (US); John R. Jacobsen, Woodbury, MN (US); Kumars Sakizadeh, Woodbury, MN (US); Zhipeng Song, Chadds Ford, PA (US); Jayshree Seth, Woodbury, MN (US); Chi-Ming Tseng, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 15/533,536

(22) PCT Filed: Dec. 14, 2015

(86) PCT No.: PCT/US2015/065517
§ 371 (c)(1),
(2) Date: Jun. 6, 2017

(87) PCT Pub. No.: WO2016/109173
PCT Pub. Date: Jul. 7, 2016

(65) Prior Publication Data
US 2017/0362467 A1 Dec. 21, 2017

Related U.S. Application Data

(60) Provisional application No. 62/097,778, filed on Dec. 30, 2014.

(51) Int. Cl.
*C09J 4/06* (2006.01)
*C09J 133/06* (2006.01)
(Continued)

(52) U.S. Cl.
CPC ............. *C09J 4/06* (2013.01); *C08F 220/06* (2013.01); *C08F 220/18* (2013.01);
(Continued)

(58) Field of Classification Search
None
See application file for complete search history.

(56) References Cited

U.S. PATENT DOCUMENTS 3,241,662 A 3/1966 Robinson
3,324,218 A 6/1967 Gebler
(Continued)

FOREIGN PATENT DOCUMENTS

EP 0301827 2/1989
EP 0372756 6/1990
(Continued)

OTHER PUBLICATIONS

Zhao, "Structured latex particles with improved mechanical properties", Progress in Organic Coatings, 1999, vol. 35, pp. 265-275.
(Continued)

*Primary Examiner* — Vu A Nguyen
(74) *Attorney, Agent, or Firm* — Jean A. Lown

(57) ABSTRACT

A pressure-sensitive adhesive is provided that is a dried product of a latex composition, which is formed from an emulsion composition. The latex composition and the emulsion composition are also provided. The emulsion composition has droplets that contain various monomers plus a (meth)acrylate polymer dissolved in the monomers. Additionally, an article containing a layer of the pressure-sensitive adhesive and a method of forming the pressure-sensitive adhesive are provided. The pressure-sensitive adhesives often have both high peel adhesion and high shear strength (i.e., high cohesive strength or high shear holding power).

15 Claims, 1 Drawing Sheet

(51) Int. Cl.
*C08L 33/02* (2006.01)
*C08F 220/06* (2006.01)
*C08F 220/18* (2006.01)
*G01N 25/48* (2006.01)

(52) U.S. Cl.
CPC ..... *C09J 133/06* (2013.01); *C08F 2220/1841* (2013.01); *C08F 2220/1858* (2013.01); *C08F 2220/1866* (2013.01); *C08F 2500/02* (2013.01); *G01N 25/4866* (2013.01)

(56) References Cited

U.S. PATENT DOCUMENTS

| | | |
|---|---|---|
| 3,578,622 A | 5/1971 | Brown |
| 4,912,169 A | 3/1990 | Whitmire |
| 5,032,460 A | 7/1991 | Kantner |
| 5,204,219 A | 4/1993 | Van Ooij |
| 5,217,805 A | 6/1993 | Kessel |
| 5,492,950 A | 2/1996 | Brown |
| 5,637,646 A | 6/1997 | Ellis |
| 5,686,517 A | 11/1997 | Wells |
| 5,686,518 A | 11/1997 | Fontenot |
| 5,804,610 A | 9/1998 | Hamer |
| 5,986,011 A | 11/1999 | Ellis |
| 6,048,611 A | 4/2000 | Lu |
| 6,451,425 B1 | 9/2002 | Kozulla |
| 6,511,744 B2 | 1/2003 | Centner |
| 6,638,637 B2 | 10/2003 | Hager |
| 6,657,011 B2 | 12/2003 | Lau |
| 6,710,128 B1 | 3/2004 | Helmer |
| 6,783,850 B2 | 8/2004 | Takizawa |
| 8,258,240 B2 | 9/2012 | Suzuki |
| 2002/0082319 A1 | 6/2002 | Zhao |
| 2003/0125459 A1 | 7/2003 | Wulff |
| 2010/0081764 A1 | 4/2010 | Ouzineb |
| 2010/0099317 A1 | 4/2010 | Suzuki |
| 2011/0008605 A1 | 1/2011 | Suzuki |
| 2011/0086219 A1 | 4/2011 | Ikeya |
| 2011/0263787 A1 | 10/2011 | Takahashi |
| 2012/0077030 A1 | 3/2012 | Gerst |
| 2012/0082816 A1 | 4/2012 | Wada |
| 2012/0114930 A1 | 5/2012 | Yamamoto |
| 2012/0157593 A1 | 6/2012 | Ootake |
| 2012/0328864 A1 | 12/2012 | Takarada |
| 2013/0005911 A1 | 1/2013 | Okamoto |
| 2013/0059105 A1 | 3/2013 | Wright |
| 2016/0333223 A1 | 11/2016 | Qie |
| 2017/0081566 A1 | 3/2017 | Zhang |

FOREIGN PATENT DOCUMENTS

| | | |
|---|---|---|
| EP | 0554832 | 8/1993 |
| EP | 1911771 | 4/2008 |
| EP | 2803712 | 11/2014 |
| JP | 2003-105298 | 4/2003 |
| JP | 2004-263024 | 9/2004 |
| JP | 2014-070122 | 4/2014 |
| WO | WO 1993/08239 | 4/1993 |
| WO | WO 1996/07522 | 3/1996 |
| WO | WO 2008/103526 | 8/2008 |
| WO | WO 2011/139593 | 11/2011 |
| WO | WO 2013/032771 | 3/2013 |
| WO | WO 2013/074446 | 5/2013 |
| WO | WO 2014/186169 | 11/2014 |
| WO | WO 2016/109174 | 7/2016 |
| WO | WO 2016/109176 | 7/2016 |

OTHER PUBLICATIONS

International Search Report for PCT International Application No. PCT/US2015/065517, dated Apr. 5, 2016, 4 pages.

WATER-BASED PRESSURE-SENSITIVE ADHESIVE COMPOSITIONS

CROSS REFERENCE TO RELATED APPLICATIONS

This application is a national stage filing under 35 U.S.C. 371 of PCT/US2015/065517, filed Dec. 14, 2015, which claims the benefit of U.S. Provisional Application No. 62/097,778, filed Dec. 30, 2014, the disclosure of which is incorporated by reference in its/their entirety herein.

TECHNICAL FIELD

A pressure-sensitive adhesive, a latex composition used to form the pressure-sensitive adhesive, and an emulsion composition used to form the latex composition are provided.

BACKGROUND

Pressure-sensitive adhesive (PSA) tapes are virtually ubiquitous in the home and workplace. In one of its simplest configurations, a pressure-sensitive tape includes a backing layer and an adhesive layer attached to the backing layer. According to the Pressure-Sensitive Tape Council, pressure-sensitive adhesives are known to possess properties including the following: (1) aggressive and permanent tack, (2) adherence with no more than finger pressure, (3) sufficient ability to hold onto an adherend, and (4) sufficient cohesive strength to be removed cleanly from the adherend. Materials that have been found to function well as PSAs include polymers designed and formulated to exhibit the requisite viscoelastic properties resulting in a desired balance of tack, peel adhesion, and shear holding power. PSAs are characterized by being normally tacky at room temperature (e.g., about 20° C. to 25° C.). Materials that are merely sticky or that adhere to a surface do not necessarily constitute a PSA; the term PSA encompasses materials with additional viscoelastic properties.

Acrylic-based pressure-sensitive adhesives have been widely used. These pressure-sensitive adhesive compositions can be prepared with or without an organic solvent. PSA compositions containing organic solvents, while currently dominant in the marketplace, are decreasing in importance due to various issues such as pollution, high energy consumption, and flammability associated with the use of organic solvents. That is, the adhesive industry is increasingly focused on adhesive compositions that have either low or no organic solvent content.

Some such adhesive compositions can, for example, be prepared from water-based latex compositions formed by emulsion polymerization. Such adhesives are described, for example, in U.S. Pat. No. 5,686,518 (Fontenot et al.), U.S. Pat. No. 6,710,128 (Helmer et al.), U.S. Pat. No. 6,511,744 (Centner et al.), U.S. Pat. No. 6,048,611 (Lu et al.), U.S. Pat. No. 4,912,169 (Whitmire et al.), U.S. Pat. No. 6,657,011 (Lau et al.), U.S. Pat. No. 8,258,240 (Suzuki et al.), and U.S. Patent Application Publication No. 2010/0081764 (Ouzineb et al.).

SUMMARY

A pressure-sensitive adhesive is provided that is the dried product of a latex composition, which is formed from an emulsion composition. The latex composition and the emulsion composition are also provided. Additionally, an article containing the pressure-sensitive adhesive and a method of forming the pressure-sensitive adhesive are provided. The pressure-sensitive adhesive often has both high peel adhesion and high shear strength (i.e., cohesion).

In a first aspect, an emulsion composition is provided that contains a) water, b) a polymerizable surfactant having an unsaturated group that can undergo free radical polymerization, c) a first monomer composition, and d) a second (meth)acrylate polymer. The first monomer composition includes 1) an alkyl (meth)acrylate having an alkyl group with at least six carbon atoms, 2) a first acidic monomer having a glass transition temperature equal to at least 100° C. when measured as a homopolymer, and 3) a second acidic monomer having a glass transition temperature no greater than 50° C. when measured as a homopolymer. The second (meth)acrylate polymer is present in an amount of 0.5 to 15 weight percent based on a total weight of monomers in the first monomer composition. The second (meth)acrylate polymer has a weight average molecular weight in a range of 3,000 to 150,000 Dalton and a glass transition temperature greater than −50° C. The second (meth)acrylate polymer is formed from a second monomer composition containing at least 10 weight percent of a non-acidic high $T_g$ monomer based on a total weight of monomers in the second monomer composition. The non-acidic high $T_g$ monomer has a glass transition temperature equal to at least 80° C. when measured as a homopolymer. The emulsion composition contains a first phase that includes water and a second phase dispersed as droplets within the first phase. The droplets contain a mixture of i) at least 85 weight percent of the first monomer composition and ii) the second (meth)acrylate polymer. The second (meth)acrylate polymer is not miscible with the first phase and is dissolved in the first monomer composition within the droplets.

In a second aspect, a latex composition is provided that contains a reaction product (i.e., polymerized product) of an emulsion composition, wherein the latex composition contains polymeric latex particles. The emulsion composition is the same as described above.

In a third aspect, a pressure-sensitive adhesive is provided that is a dried product of a latex composition. The latex composition contains a reaction product (i.e., polymerized product) of an emulsion composition, wherein the latex composition contains polymeric latex particles. The emulsion composition is the same as described above.

In a fourth aspect, an article is provided. The article contains a substrate and a first pressure-sensitive adhesive layer positioned adjacent to (and adhered directly or indirectly to) a first major surface of the substrate. The pressure-sensitive adhesive layer is a dried product of a latex composition. The latex composition contains a reaction product (i.e., polymerized product) of an emulsion composition, wherein the latex composition contains polymeric latex particles. The emulsion composition is the same as described above.

In a fifth aspect, a method of forming a pressure-sensitive adhesive is provided. The method includes a) forming an emulsion composition as described above; b) polymerizing the emulsion composition to form a latex composition comprising polymeric latex particles; and c) drying the latex composition to form the pressure-sensitive adhesive.

DETAILED DESCRIPTION

Figure 1:
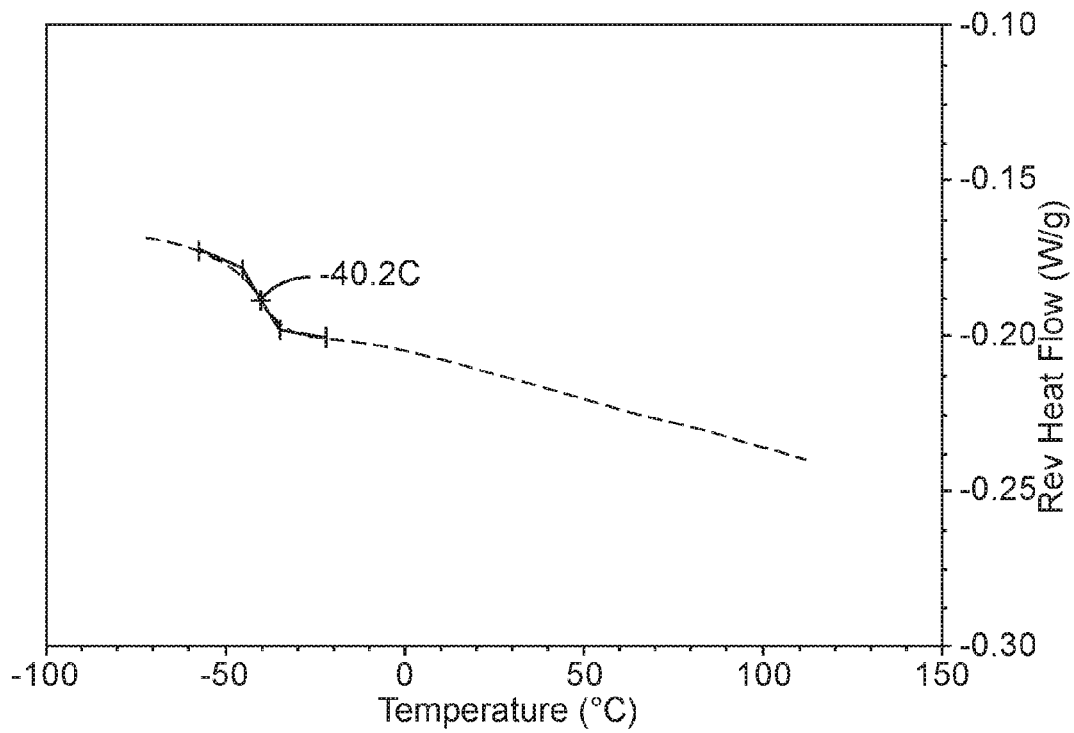
FIG. 1 is a plot of reversible heat flow (obtained during the second heating cycle using Modulated Differential Scanning calorimetry) versus temperature for the dry polymeric material of Example 9.

A pressure-sensitive adhesive is provided that is a dried product of a latex composition, which is formed from an emulsion composition. The latex composition and the emulsion composition are also provided. The emulsion composition has droplets suspended in a first phase that is mainly water. The droplets contain various monomers plus a (meth)acrylate polymer dissolved in the monomers. The content of the droplets in the emulsion composition are polymerized to form polymeric latex particles in the latex composition. A pressure-sensitive adhesive is provided by drying the latex composition. Additionally, an article containing a layer of the pressure-sensitive adhesive and a method of forming the pressure-sensitive adhesive are provided. The pressure-sensitive adhesives often have both high peel adhesion (i.e., peel strength) and high shear strength (i.e., high cohesive strength or high shear holding power).

As used herein, the terms "polymer" and "polymeric" and "polymeric material" are used interchangeably to refer to a homopolymer, copolymer, terpolymer, and the like.

As used herein, the term "(meth)acrylate" refers to both methacrylate and acrylate monomers, polymeric materials derived from these monomers, or both. Likewise, the term "(meth)acrylic" refers to both acrylic and methacrylic materials, the term "(meth)acrylamide" refers to both acrylamide and methacrylamide, and the term "(meth)acrylonitrile" refers to both methacrylonitrile and acrylonitrile.

As used herein, the term "(meth)acrylate polymer" refers to a polymeric material formed from one or more ethylenically unsaturated monomers, wherein greater than 50 weight percent of the monomers have an ethylenically unsaturated group that is a (meth)acryloyl group of formula $H_2C=CR^a-(CO)-$ where $R^a$ is hydrogen or methyl and $-(CO)-$ is a carbonyl group. Some example (meth)acrylate polymers are formed from monomer compositions having greater than 60 weight percent, greater than 70 weight percent, greater than 80 weight percent, greater than 90 weight percent, greater than 95 weight percent, greater than 98 weight percent, or greater than 99 weight percent monomers having a (meth)acryloyl group. The weight percent is based on the total weight of monomers in the monomer composition used to form the (meth)acrylate polymer.

The term "glass transition temperature" or "$T_g$" refers to the temperature at which a material changes from a glassy state to a rubbery state. In this context, the term "glassy" means that the material is hard and brittle (and therefore relatively easy to break) while the term "rubbery" means that the material is elastic and flexible. For polymeric materials, the $T_g$ is the critical temperature that separates their glassy and rubbery behaviors. If a polymeric material is at a temperature below its $T_g$, large-scale molecular motion is severely restricted because the material is essentially frozen. On the other hand, if the polymeric material is at a temperature above its $T_g$, molecular motion on the scale of its repeat unit takes place, allowing it to be soft or rubbery. Any reference herein to the $T_g$ of a monomer refers to the $T_g$ of a homopolymer formed from that monomer. The glass transition temperature of a polymeric material is often determined using methods such as Differential Scanning calorimetry (e.g., Modulated Differential Scanning calorimetry). Alternatively, the glass transition of a polymeric material can be calculated using the Fox Equation if the amount and $T_g$ of each monomer used to form the polymeric material are known.

When referring to a range, the endpoints of the range are considered to be in the range. For example, the expressions "in a range from x to y", "in a range of x to y", "in an amount from x to y", "in an amount of x to y", or similar expressions include the endpoints x and y.

As used herein, the term "and/or" such as in the expression A and/or B means A alone, B alone, or both A and B.

The emulsion composition that is used to form the latex composition and, ultimately, the pressure-sensitive adhesive contains a) water, b) a polymerizable surfactant having an unsaturated group that can undergo a free radical polymerization reaction (e.g., an ethylenically unsaturated group), c) a first monomer composition, and d) a second (meth)acrylate polymer. The emulsion has a first phase that includes water and a second phase dispersed as droplets within the first phase. The polymerizable surfactant is typically predominately (e.g., at least 95 weight percent or more, at least 97 weight percent, at least 98 weight percent, at least 99 weight percent, at least 99.5 weight percent, at least 99.8 weight percent, or at least 99.9 weight percent) present in the first phase and/or at the interface between the droplets and the first phase. The second (meth)acrylate polymer is dissolved in the monomers of the first monomer composition within the droplets of the second phase of the emulsion composition. The second (meth)acrylate polymer typically is not miscible with the first phase of the emulsion composition. The second (meth)acrylate polymer is formed from a second monomer composition that is different than the first monomer composition contained in the emulsion composition.

A major component of the emulsion composition is water. The percent solids of the emulsion composition are often up to 70 weight percent or higher such as up to 75 weight percent. If the percent solids are higher, the viscosity of the emulsion may be too high to adequately disperse the droplets. In some embodiments, the percent solids are up to 65 weight percent, up to 60 weight percent, up to 55 weight percent, or up to 50 weight percent. The percent solids are typically at least 10 weight percent. If the solids are lower, the efficiency of preparation of the latex particles may be unacceptably low. In some embodiments, the percent solids are at least 15 weight percent, at least 20 weight percent, at least 25 weight percent, at least 30 weight percent, at least 35 weight percent, at least 40 weight percent, or at least 45 weight percent. In some examples, the percent solids are in a range of 10 to 75 weight percent, in a range of 10 to 70 weight percent, 20 to 70 weight percent, 30 to 70 weight percent, 40 to 70 weight percent, or 40 to 60 weight percent. The percent solids are based on the total weight of the emulsion composition.

The portion of the emulsion composition that is not a solid is typically water. Thus, the water content of the emulsion is often at least 25 weight percent or at least 30 weight percent. In some embodiments, the water content can be up to 90 weight percent, up to 85 weight percent, up to 80 weight percent, up to 75 weight percent, up to 70 weight percent, up to 65 weight percent, up to 60 weight percent, or up to 55 weight percent. The water content can be at least 35 weight percent, at least 40 weight percent, at least 45 weight percent, or at least 50 weight percent. In some examples, the water content is in a range of 25 to 90 weight percent, in a range of 30 to 90 weight percent, 30 to 80 weight percent, 30 to 70 weight percent, 30 to 60 weight percent, or 40 to 60 weight percent. The amount of water is based on the total weight of the emulsion composition.

Some of the water can be replaced with a polar organic solvent that is miscible with water. If present, no more than 20 weight percent, no more than 15 weight percent, no more than 10 weight percent, or no more than 5 weight percent of the first phase is the water-miscible, polar organic solvent. The polar organic solvent is often an alcohol such as an alcohol having 1 to 10 carbon atoms, 1 to 6 carbon atoms, or 1 to 4 carbon atoms. In many embodiments, no water-miscible, polar organic solvent is purposefully added to the emulsion composition but may be present as a contaminant or diluent in one of the other components.

The emulsion composition contains a polymerizable surfactant. As used herein, the term "polymerizable surfactant" refers to a surfactant with a polymerizable group, which is an unsaturated group that can undergo a free radical polymerization reaction. In the emulsion composition, the polymerizable surfactant is typically in the first phase and/or at the interface between first phase and the droplets that are suspended in the first phase. The polymerizable surfactant facilitates the formation of a latex composition having good stability (e.g., the polymeric latex particles remain suspended and do not coalesce). The polymerizable surfactant may become part of the polymeric latex particles during the polymerization reaction of the emulsion composition.

Using a polymerizable surfactant rather than a surfactant without a polymerizable group tends to improve the peel strength and the shear strength of the resulting pressure-sensitive adhesive. Under high humidity conditions, a surfactant without a polymerizable group tends to migrate to the surface of a pressure-sensitive adhesive. The presence of the surfactant on the surface of the pressure-sensitive adhesive can decrease the adhesive properties of the pressure-sensitive adhesive. In contrast, the polymerizable surfactant can polymerize with the monomers in the first monomer composition and become part of the polymeric latex particles. Polymerization into the polymeric latex particle tends to restrict the mobility of the surfactant.

Example polymerizable surfactants include propenyl polyoxyethylene alkylphenyl compounds such as those commercially available from Montello, Inc. (Tulsa, Okla., USA) under the trade designation NOIGEN RN (e.g., RN-10, RN-20, RN-30, RN-40, and RN-5065), which have a structure shown below where n is at least 2 and where x is an integer such as one close to or equal to 9.

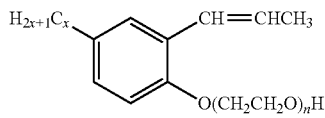

Other example polymerizable surfactants include propenyl polyoxyethylene alkylphenyl ether ammonium sulfate compounds such as those commercially available from Montello, Inc. under the trade designation HITENOL BC (e.g., BC-10, BC-1025, BC-20, BC-2020, and BC-30), which have a structure shown below where n is at least 2 and where x is an integer such as one close to or equal to 9.

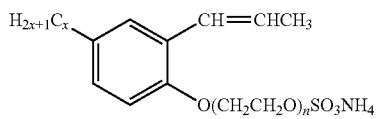

Another example polymerizable surfactant is sodium dodecylallyl sulfosuccinate, $CH_3—(CH_2)_{11}—O—(CO)—CH_2—CH(SO_3Na)—(CO)—O—CH_2—CH=CH_2$, which may be commercially available under the trade designation TREM LF40 from Cognis Corporation (North Rhime-Westphalia, Germany). Yet other example polymerizable surfactants are phosphate esters such as those commercially available from Croda (Edison, N.Y., USA) under the trade designation MAXENUL (e.g., MAXEMUL 6106 and 6112).

The polymerizable surfactant is typically used in an amount up to about 2 weight percent, up to 1.8 weight percent, or up to 1.5 weight percent. The amount of the polymerizable surfactant is usually at least 0.5 weight percent, at least 0.7 weight percent, or at least 1 weight percent. The weight percents are based on the total weight of monomers in the first monomer composition.

The emulsion composition contains a first monomer composition. The first monomer composition is typically selected such that the polymerized product of the first monomer composition, which is referred to as the "first (meth)acrylate polymer", has a glass transition temperature no greater than 20° C., no greater than 10° C., no greater than 0° C., no greater than −10° C., or no greater than −20° C.

The first monomer composition in the emulsion composition typically includes 1) an alkyl (meth)acrylate having an alkyl group with at least six carbon atoms, 2) a first acidic monomer having a glass transition temperature equal to at least 100° C. when measured as a homopolymer, and 3) a second acidic monomer having a glass transition temperature no greater than 50° C. when measured as a homopolymer. While most, if not all, of the alkyl (meth)acrylate is within the droplets of the emulsion, the two acidic monomers are likely to be distributed both within the droplet and within the first phase (i.e., water phase). That is, the alkyl (meth)acrylate monomer is likely to have a low solubility in the first phase and is likely to be predominately (e.g., at least 95 weight percent or more, at least 97 weight percent, at least 98 weight percent, at least 99 weight percent, at least 99.5 weight percent, at least 99.8 weight percent, or at least 99.9 weight percent) in the droplets, which are dispersed in the first phase. The acidic monomers typically have greater solubility in water compared to the alkyl (meth)acrylate monomer. As polymerization occurs within the droplet, some of the acidic monomer in the first phase may diffuse into the droplet and become part of polymeric latex particles that are formed.

The alkyl (meth)acrylate in the first monomer composition has an alkyl group with at least six carbon atoms. The alkyl group can be linear, branched, cyclic, or a combination thereof. The alkyl (meth)acrylate having an alkyl group with at least six carbon atoms is sufficiently hydrophobic to reside predominately (e.g., at least 95 weight percent or more, at least 97 weight percent, at least 98 weight percent, at least 99 weight percent, at least 99.5 weight percent, at least 99.8 weight percent, or at least 99.9 weight percent) in the droplets within the emulsion composition. Alkyl (meth) acrylate monomers with an alkyl group having less than six carbon atoms are less hydrophobic and are less likely to reside predominately within the droplets. In some embodiments, the alkyl group can have at least 8 carbon atoms, at least 10 carbon atoms, or at least 12 carbon atoms. The alkyl group of the alkyl (meth)acrylate can have up to 28 carbon atoms or more, up to 24 carbon atoms, up to 20 carbon atoms, or up to 18 carbon atoms. In many embodiments, particularly when the number of carbon atoms is greater than 12, the alkyl group is branched. Some alkyl (meth)acrylates having an alkyl group greater than 12 carbon atoms can crystallize if the alkyl group is linear. Crystallization of the alkyl (meth)acrylate is not desirable in the emulsion composition.

Example alkyl (meth)acrylate monomers having an alkyl group with at least six carbon atoms for use in the first monomer composition include, but are not limited to, n-hexyl acrylate, cyclohexyl acrylate, 4-methyl-2-pentyl acrylate, 3-methylpentyl acrylate, 2-ethylbutyl acrylate, 2-ethylhexyl acrylate, 2-methylhexyl acrylate, n-octyl acrylate, isooctyl acrylate, 2-octyl acrylate, isononyl acrylate, isoamyl acrylate, isobornyl acrylate, n-decyl acrylate, isodecyl acrylate, 2-propylheptyl acrylate, isotridecyl acrylate, isostearyl acrylate, 2-octyldecyl acrylate, lauryl acrylate, heptadecanyl acrylate, n-hexyl methacrylate, isodecyl methacrylate, 2-ethylhexyl methacrylate, isooctyl methacrylate, isobornyl methacrylate, and lauryl methacrylate.

Still other alkyl (meth)acrylates having a linear or branched alkyl group with at least six carbon atoms for use in the first monomer composition are of Formula (I).

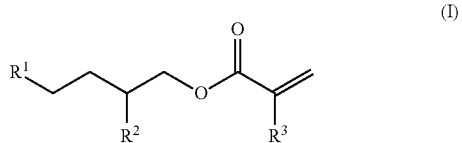

In Formula (I), group $R^3$ is hydrogen or methyl and groups $R^1$ and $R^2$ are each independently a linear or branched alkyl group having 4 to 14 carbon atoms. These monomers are often formed from a Guerbet alcohol, which is a 2-alkyl alkanol. Example monomers of Formula (I) include 2-butyloctyl acrylate, 2-butyldecyl acrylate, 2-hexyloctyl acrylate, 2-hexyldecyl acrylate, 2-tetradecyloctadecyl acrylate, 2-dodecylhexadecyl acrylate, 2-decyltetradecyl acrylate, 2-octyldodecyl acrylate, 2-hexyldecyl acrylate, 2-octyldecyl acrylate, 2-hexyldodecyl acrylate, and 2-octyldodecyl acrylate.

The first monomer composition typically contains at least 65 weight percent alkyl (meth)acrylate having an alkyl group with at least six carbon atoms. The first monomer composition often contains at least 70 weight percent, at least 75 weight percent, at least 80 weight percent, at least 85 weight percent, or at least 90 weight percent of the alkyl (meth)acrylate having an alkyl group with at least six carbon atoms. The amount of the alkyl (meth)acrylate having an alkyl group with at least six carbon atoms can be up to 97 weight percent. If the concentration is higher, there will be an insufficient amount of the acidic monomers present and/or the cohesive strength of the final polymeric material may be insufficiently low. The first monomer composition often contains up to 96 weight percent, up to 95 weight percent, or up to 94 weight percent alkyl (meth)acrylate. In some embodiments, the amount of the alkyl (meth)acrylate is in a range of 65 to 97 weight percent, in a range of 70 to 97 weight percent, in a range of 75 to 97 weight percent, in a range of 80 to 97 weight percent, in a range of 85 to 97 weight percent, in a range of 88 to 97 weight percent, or in a range of 90 to 97 weight percent. The amount of the alkyl (meth)acrylate is based on a total weight of monomers in the first monomer composition.

In addition to the alkyl (meth)acrylate having an alkyl group with at least six carbon atoms, the first monomer composition includes two acidic monomers. The first acidic monomer has a $T_g$ equal to at least 100° C. when measured as a homopolymer using Differential Scanning calorimetry. In some embodiments, the $T_g$ is equal to at least 120° C., at least 140° C., at least 160° C., or at least 180° C. The first acidic monomer tends to increase the cohesive strength of the final polymeric material. Suitable first acidic monomers include, for example, methacrylic acid, acrylic acid, itaconic acid, maleic anhydride (which undergoes hydrolysis to form two carboxylic acid groups), and maleic acid. In many embodiments, the first acidic monomer is acrylic acid or methacrylic acid.

The first monomer composition typically contains at least 0.5 weight percent of the first acidic monomer. If the amount of the first acidic monomer is less, the cohesive strength of the final pressure-sensitive adhesive may be unacceptably low. The first monomer composition often contains at least 1 weight percent, at least 1.5 weight percent, or at least 2 weight percent of the first acidic monomer. The amount of the first acidic monomer can be up to 5 weight percent. If the amount of the first acidic monomer is greater, the amount of this monomer present in the first phase may be unacceptably high. This can lead to poor latex composition stability and to coagulation of the polymeric latex particles. Further, the peel strength of the resulting pressure-sensitive adhesive may be unacceptably low. The amount of the first acidic monomer is often up to 4.5 weight percent, up to 4 weight percent, up to 3.5 weight percent, or up to 3 weight percent. For example the amount of the first acidic monomer can be in a range of 0.5 to 5 weight percent, 1 to 5 weight percent, or 2 to 5 weight percent. The amount of the first acidic monomer is based on a total weight of monomers in the first monomer composition.

The second acidic monomer in the first monomer composition has a $T_g$ no greater than 50° C. when measured as a homopolymer using Differential Scanning calorimetry. In some embodiments, the $T_g$ is no greater than 40° C., no greater than 30° C., or no greater than 20° C. Suitable first acidic monomers include, for example, carboxyethyl acrylate and mono-2-acryloyloxyethyl succinate.

The first monomer composition typically contains at least 1 weight percent of the second acidic monomer. If the amount of the second acidic monomer is less, the resulting pressure-sensitive adhesive may not have an appropriate balance between peel strength and cohesive strength. Further, the second acidic monomer tends to be less hydrophilic (more hydrophobic) than the first acidic monomer and can facilitate drawing the first acidic monomer into the droplets within the emulsion composition and/or facilitate drawing the first acidic monomer into the polymeric latex particles during polymerization. If the amount of the second acidic monomer is too low, the amount of the first acidic monomer within the droplets may also be too low. The first monomer composition often contains at least 2 weight percent, at least 3 weight percent, or at least 4 weight percent of the second acidic monomer. The amount of the second acidic monomer can be up to 10 weight percent. If the amount of the second acidic monomer is greater, the resulting polymeric latex particles may tend to coagulate. Further, the peel strength of the resulting pressure-sensitive adhesive may be unacceptably low. The amount of the second acidic monomer is often up to 8 weight percent, up to 6 weight percent, up to 5 weight percent, or up to 4 weight percent. For example the amount of the second acidic monomer can be in a range of 1 to 10 weight percent, 2 to 10 weight percent, 1 to 8 weight percent, 2 to 8 weight percent, 1 to 6 weight percent, 2 to 6 weight percent, 1 to 5 weight percent, or 2 to 5 weight percent. The amount of the second acidic monomer is based on a total weight of monomers in the first monomer composition.

The first monomer composition optionally can contain up to 20 weight percent alkyl (meth)acrylates having an alkyl group with one to five carbon atoms. The alkyl group can be linear or branched. If larger amounts of an alkyl (meth)acrylate having an alkyl group with one to five carbon atoms are used, too much of the overall first monomer composition may be in the first phase rather than in the droplets. In many embodiments, the amount of alkyl (meth)acrylate having an alkyl group with one to five carbon atoms is present in an amount no greater than 15 weight percent, no greater than 10 weight percent, or no greater than 5 weight percent. In some embodiments, there is no alkyl (meth)acrylate having an alkyl group with one to five carbon atoms. In other embodiments, the first monomer composition can contain at least 0.5 weight percent, at least 1 weight percent, at least 2 weight percent, or at least 5 weight percent of the alkyl (meth)acrylate having an alkyl group with one to five carbon atoms. The amount of the alkyl (meth)acrylate with an alkyl group having one to five carbon atoms is usually in a range of 0 to 20 weight percent, 1 to 20 weight percent, 5 to 20 weight percent, 10 to 20 weight percent, 0 to 15 weight percent, 1 to 15 weight percent, 5 to 15 weigh percent, 0 to 10 weight percent, 1 to 10 weight percent, 0 to 5 weight percent, or 1 to 5 weight percent. The amount of the alkyl (meth)acrylate is based on a total weight of monomers in the first monomer composition.

The first monomer composition can contain 65 to 98.5 weight percent of the alkyl (meth)acrylate having an alkyl group with at least six carbon atoms, 0 to 20 weight percent of the alkyl (meth)acrylate having an alkyl group with one to five carbon atoms, 0.5 to 5 weight percent of the first acidic monomer, and 1 to 10 weight percent of the second acidic monomer. In some examples, the first monomer composition contains 70 to 98 weight percent of the alkyl (meth)acrylate having an alkyl group with at least six carbon atoms, 0 to 15 weight percent of the alkyl (meth)acrylate having an alkyl group with one to five carbon atoms, 0.5 to 5 weight percent of the first acidic monomer, and 1 to 10 weight percent of the second acidic monomer. In some examples, the first monomer composition contains 70 to 97 weight percent of the alkyl (meth)acrylate having an alkyl group with at least six carbon atoms, 0 to 15 weight percent of the alkyl (meth)acrylate having an alkyl group with one to five carbon atoms, 0.5 to 5 weight percent of the first acidic monomer, and 1 to 10 weight percent of the second acidic monomer. In other examples, the first monomer composition contains 75 to 97 weight percent of the alkyl (meth)acrylate having an alkyl group with at least six carbon atoms, 0 to 10 weight percent of the alkyl (meth)acrylate having an alkyl group with one to five carbon atoms, 0.5 to 5 weight percent of the first acidic monomer, and 1 to 10 weight percent of the second acidic monomer. In yet other examples, the first monomer composition contains 80 to 97 weight percent of the alkyl (meth)acrylate having an alkyl group with at least six carbon atoms, 0 to 5 weight percent of the alkyl (meth)acrylate having an alkyl group with one to five carbon atoms, 0.5 to 5 weight percent of the first acidic monomer, and 1 to 10 weight percent of the second acidic monomer.

The first monomer composition often contains 85 to 98.5 weight percent of the alkyl (meth)acrylate having an alkyl group with at least six carbon atoms, 0.5 to 5 weight percent of the first acidic monomer, and 1 to 10 weight percent of the second acidic monomer. In some examples, the first monomer composition contains 85 to 97 weight percent of the alkyl (meth)acrylate having an alkyl group with at least six carbon atoms, 0.5 to 4 weight percent of the first acidic monomer, and 1 to 8 weight percent of the second acidic monomer. In other examples, the first monomer composition contains 88 to 97 weight percent of the alkyl (meth)acrylate having an alkyl group with at least six carbon atoms, 1 to 4 weight percent of the first acidic monomer, and 2 to 8 weight percent of the second acidic monomer. In still other embodiments, the first monomer composition contains 90 to 97 weight percent of the alkyl (meth)acrylate having an alkyl group with at least six carbon atoms, 1 to 4 weight percent of the first acidic monomer, and 2 to 6 weight percent of the second acidic monomer. The amount of each monomer is based on a total weight of monomers in the first monomer composition.

The emulsion composition has droplets dispersed in the first phase. Prior to polymerization of the emulsion composition to form a latex composition, the droplets contain a second (meth)acrylate polymer dissolved in the components of the first monomer composition that are in the droplets. Typically, at least 85 weight percent of the monomers in the first monomer composition are within the droplets of the emulsion and no more than 15 weight percent of the monomers of the first composition are within the first phase of the emulsion composition. Polar monomers such as the first acidic monomer and the second acidic monomer and other monomers that are less hydrophobic than the alkyl (meth)acrylate having an alkyl group with at least six carbon atoms (such as alkyl (meth)acrylate monomers having an alkyl group with one to five carbon atoms) may be distributed within both the droplets and the first phase. As polymerization proceeds, these monomers in the first phase may diffuse into the droplets and become part of the polymeric latex particles. In some embodiments, at least 92 weight percent, at least 95 weight percent, at least 98 weight percent, or at least 99 weight percent of the monomers in the first monomer composition are in the droplets of the emulsion composition.

The second (meth)acrylate polymer is selected so that is can be dissolved in the first monomer composition within the droplets of the emulsion composition and so that it is not miscible with the first phase. The second (meth)acrylate polymer is formed prior to dissolution by the components of the first monomer composition within the droplets. The second (meth)acrylate polymer facilitates the formation of stable droplets within the first phase of the emulsion composition.

The second (meth)acrylate polymer is typically formed from a second monomer composition. The second monomer composition is selected to provide a second (meth)acrylate polymer that can be dissolved in the first monomer composition. The second monomer composition is not identical to the first monomer composition. Additionally, it is often desirable that the second (meth)acrylate polymer be distributed fairly uniformly throughout the droplets within the emulsion composition. That is, it is often desirable that the second (meth)acrylate polymer and the polymeric material formed by polymerization of the first monomer composition (i.e., the first (meth)acrylate polymer) are both fairly uniformly distributed throughout the resulting polymeric latex particles even though their compositions are not identical. The first (meth)acrylate polymer and the second (meth)acrylate polymer are within the same latex particles.

The second monomer composition is selected to provide a second (meth)acrylate polymer that has a glass transition temperature greater than −50° C. as measured using Differential Scanning calorimetry (e.g., Modulated Differential calorimetry). For example, the glass transition temperature can be greater than −40° C., greater than −30° C., greater than −20° C., greater than −10° C., greater than 0° C. The grass transition temperature can be up to 120° C. or even higher, up to 100° C., up to 80° C., up to 60° C., up to 40° C., or up to 20° C.

The second monomer composition used to form the second (meth)acrylate polymer typically includes a non-acidic monomer having a glass transition temperature greater than 80° C. when polymerized as a homopolymer. This monomer, which can be referred to as a "non-acidic high $T_g$ monomer", can be the only monomer in the second monomer composition or it can be combined with other optional monomers. As the name implies, this monomer does not contain an acidic group such as a carboxyl group (—COOH). The non-acidic high $T_g$ monomer typically does not include an aromatic ring (e.g., the non-acidic high $T_g$ monomer is not styrene, a styrene derivative, an aryl (meth)acrylate, or an aryl (meth)acrylate derivative).

The non-acidic high $T_g$ monomer is often an alkyl (meth)acrylate having a cyclic alkyl group with 6 to 12 carbon atoms. As used herein, the term "cyclic alkyl" refers to a mono-cyclic alkyl, a bicyclic alkyl, or a tricyclic alkyl. Examples include, but are not limited to, isobornyl (meth)acrylate, 3,3,5-trimethylcyclohexyl methacrylate, cyclohexyl methacrylate, 3,5-dimethyladamantyl acrylate, and 4-tert-butylcylcohexyl methacrylate.

In other embodiments, the non-acidic high $T_g$ monomer can be an alkyl methacrylate having a linear or branched alkyl group with 1 to 4 carbon atoms. If there are more than two carbon atoms, the alkyl is typically branched. Example monomers include methyl methacrylate, ethyl methacrylate, isopropyl methacrylate, isobutyl methacrylate, and tert-butyl methacrylate.

In still other embodiments, the non-acidic high $T_g$ monomer is acrylamide, (meth)acrylonitrile, an N-alkyl acrylamide having an alkyl group with 1 to 10 carbon atoms (e.g., 2 to 10 carbon atoms or 4 to 10 carbon atoms) such as N-octyl acrylamide, N-isopropyl acrylamide, N-tert-butyl acrylamide, or an N,N-dialkyl acrylamide having alkyl groups with 1 to 10 carbon atoms (e.g., 1 to 6 carbon atoms or 1 to 4 carbon atoms) such as N,N-dimethyl acrylamide.

The second monomer composition contains at least 10 weight percent of the non-acidic high $T_g$ monomer based on the total weight of monomers in the second monomer composition. In some embodiments, the amount of the non-acidic high $T_g$ monomer in the second monomer composition can be at least 20 weight percent, at least 30 weight percent, at least 40 weight percent, or at least 50 weight percent. The non-acidic high $T_g$ monomer can be the only monomer in the second monomer composition. That is, the second monomer composition can contain 100 weight percent of the non-acidic high $T_g$ monomer provided that the resulting second (meth)acrylate is not miscible in the first phase. The amount of the non-acidic high $T_g$ monomer is often up to 97 weight percent, up to 95 weight percent, up to 90 weight percent, up to 85 weight percent, up to 80 weight percent, up to 75 weight percent, or up to 70 weight percent. The weight percent is based on the total weight of monomers in the second monomer composition.

If the non-acidic high $T_g$ monomer is an alkyl (meth)acrylate having a cyclic alkyl group with 6 to 12 carbon atoms and/or an alkyl methacrylate having a linear or branched alkyl group with 1 to 4 carbon atoms, this monomer can be used in any amount up to 100 weight percent based on a total weight of monomers in the second monomer composition.

If the non-acidic high $T_g$ monomer is an acrylamide, (meth)acrylonitrile, N-alkyl acrylamide, N,N-dialkylacrylamide, or a combination thereof, this monomer can be used in amounts up to 20 weight percent or up to 15 weight percent based on the total weight of monomers in the second monomer composition. If used in larger amounts, the resulting second (meth)acrylate polymer may be partially miscible with the first phase and/or may migrate to the outer portions of the droplets resulting in non-uniform distribution of the second (meth)acrylate polymer throughout the droplets. If higher amounts of the non-acidic high $T_g$ monomer is desired, these monomers can be combined with an alkyl (meth)acrylate having a cyclic alkyl group with 6 to 12 carbon atoms and/or with an alkyl methacrylate having a linear or branched alkyl group with 1 to 4 carbon atoms.

In some embodiments, the non-acidic high $T_g$ monomer used in the second monomer composition is a mixture of a first non-acidic high $T_g$ monomer and a second non-acidic high $T_g$ monomer. The first non-acidic high $T_g$ monomer is selected from an alkyl (meth)acrylate having a cyclic alkyl group with 6 to 12 carbon atoms, an alkyl methacrylate having a linear or branched alkyl group with 1 to 4 carbon atoms, or a mixture thereof. The second non-acidic high $T_g$ monomer is selected from acrylamide, (meth)acrylonitrile, N-alkyl acrylamide having an alkyl group with 1 to 10 carbon atoms, N,N-dialkyl acrylamide having alkyl groups with 1 to 10 carbon atoms, and a mixture thereof.

The second monomer composition often contains 10 to 100 weight percent of the non-acidic high $T_g$ monomer and 0 to 90 weight percent of other optional monomers. These other optional monomers have a $T_g$ that is no greater than 80° C. and/or have an acidic group. In some examples, the second monomer composition contains 15 to 100 weight percent of the non-acidic high $T_g$ monomer and 0 to 85 weight percent of other optional monomers, 15 to 97 weight percent of the non-acidic high $T_g$ monomer and 3 to 85 weight percent of the optional monomers, 15 to 95 weight percent of the non-acidic high $T_g$ monomer and 5 to 85 weight percent of the optional monomers, 15 to 85 weight percent of the non-acidic high $T_g$ monomer and 15 to 85 weight of the optional monomers, or 20 to 75 weight percent of the non-acidic high $T_g$ monomer and 25 to 80 weight percent of the optional monomers. The weight percent are based on the total weight of monomers in the second monomer composition.

One of the optional monomers that can be combined with the non-acidic high $T_g$ monomer in the second monomer composition is an alkyl acrylate such as those having a linear or branched alkyl group with at least four carbon atoms. These monomers often have a $T_g$ that is no greater than 50° C., no greater than 20° C., or no greater than 0° C. when measured as a homopolymer using Differential Scanning calorimetry. While small amounts of alkyl acrylate monomers with alkyl groups having less than four carbon atoms can be used, these monomers can facilitate the migration of the second (meth)acrylate polymer to the interface between the droplets and the first phase within the emulsion composition. In many embodiments, the alkyl group of the alkyl acrylate monomer has at least six carbon atoms or at least 8 carbon atoms. The alkyl group of the alkyl acrylate monomer can have, for example, up to 13 carbon atoms. In many embodiments, the alkyl group can have up to 12 carbon atoms, up to 10 carbon atoms, or up to 8 carbon atoms. Suitable alkyl acrylates having a linear or branched alkyl group with at least four carbon atoms for use in the second monomer composition include, but are not limited to, n-butyl acrylate, isobutyl acrylate, n-pentyl acrylate, isopentyl acrylate, 2-methylbutyl acrylate, n-hexyl acrylate, 4-methyl-2-pentyl acrylate, 2-ethylhexyl acrylate, 2-methylhexyl acrylate, n-octyl acrylate, isooctyl acrylate, 2-octyl acrylate, isononyl acrylate, isoamyl acrylate, n-decyl acrylate, isodecyl acrylate, 2-propylheptyl acrylate, isotridecyl acrylate, and lauryl acrylate.

Another optional monomer that can be combined with the non-acidic high $T_g$ monomer in the second monomer composition is an alkyl methacrylate having a linear or branched alkyl group with at least five carbon atoms. These monomers often have a $T_g$ that is no greater than 50° C., no greater than 20° C., or no greater than 0° C. when measured as a homopolymer using Differential Scanning calorimetry. The alkyl group of the alkyl methacrylate can have up to 13 carbon atoms, up to 12 carbon atoms, or up to 10 carbon atoms and can have at least 5 or 6 carbon atoms. Suitable alkyl methacrylates include, for example, n-hexyl methacrylate, isodecyl methacrylate, 2-ethylhexyl methacrylate, isooctyl methacrylate, and lauryl methacrylate.

The amount of the alkyl acrylate having a linear or branched alkyl group with at least four carbon atoms and/or the amount of the alkyl methacrylate having a linear or branched alkyl group with at least five carbon atoms in the second monomer composition can be in a range of 0 to 90 weight percent based on the total weight of monomers in the second monomer composition. This optional monomer can improve the compatibility between the second (meth)acrylate polymer and the first monomer composition. If present, the amount of the alkyl acrylate and/or alkyl methacrylate is often at least 1 weight percent, at least 2 weight percent, or at least 5 weight percent. The amount of the alkyl acrylate monomer and/or alkyl methacrylate can be at least 10 weight percent, at least 15 weight percent, at least 20 weight percent, at least 25 weight percent, or at least 30 weight percent. If the amount of the alkyl acrylate and/or alkyl methacrylate is greater than 90 weight percent, the resulting (meth)acrylate polymer may have an insufficient amount of the non-acidic high $T_g$ monomer and the glass transition temperature may be lower than desired. In some embodiments, the amount of the alkyl acrylate and/or alkyl methacrylate is up to 85 weight percent, up to 80 weight percent, up to 75 weight percent, up to 70 weight percent, up to 60 weight percent, up to 50 weight percent, or up to 40 weight percent.

The second monomer composition can optionally include a polar monomer such as an optional acid-containing monomer (i.e., a monomer with an acidic group) or an optional hydroxyl-containing monomer (i.e., a monomer with a hydroxyl group). These optional monomers can be added to further enhance the compatibility of the resulting second (meth)acrylate polymer with the first monomer composition within the droplets of the emulsion composition. Suitable optional acid-containing monomers include, but are not limited to, (meth)acrylic acid, itaconic acid, maleic acid, 2-carboxyethyl acrylate, crotonic acid, citraconic acid, maleic acid, maleic anhydride (which hydrolyzes to have two carboxylic acid groups), oleic acid, and mono-2-acryloyloxyethyl succinate. Suitable optional hydroxyl-containing monomers include, but are not limited to, hydroxyalkyl (meth)acrylates (e.g., 2-hydroxyethyl (meth)acrylate, 2-hydroxypropyl (meth)acrylate, 3-hydroxypropyl (meth)acrylate, and 4-hydroxybutyl (meth)acrylate), or hydroxyalkyl (meth)acrylamides (e.g., 2-hydroxyethyl (meth)acrylamide or 3-hydroxypropyl (meth)acrylamide). In many embodiments, the optional polar monomer has a (meth)acryloyl group. The second monomer composition typically contains 0 to 10 weight percent, 0 to 8 weight percent, 0 to 6 weight percent, 0 to 5 weight percent, 0 to 4 weight percent, or 0 to 2 weight percent of the optional acid-containing monomer and/or optional hydroxyl-containing monomer. The weight percents are based on the total weight of monomers within the second monomer composition.

Still other optional monomers can be included in the second monomer composition provided that there is suitable compatibility between the resulting second (meth)acrylate polymer and first monomer composition within the emulsion composition and provided that the second (meth)acrylate polymer can be dissolved within the droplets of the emulsion composition. Example optional monomers include various vinyl monomers, wherein the vinyl group is not a (meth)acryloyl group. Optional vinyl monomers include, for example, vinyl esters such as vinyl butyrate, and various vinyl non-aromatic heterocyclic monomers such as N-vinyl pyrollidone and N-vinyl caprolactam. The second monomer composition typically contains 0 to 10 weight percent, 0 to 8 weight percent, 0 to 6 weight percent, 0 to 5 weight percent, 0 to 4 weight percent, or 0 to 2 weight percent of the optional monomer having a vinyl group that is not a (meth)acryloyl group. The weight percents are based on the total weight of monomers within the second monomer composition.

A crosslinking monomer typically is not included in the second monomer composition. A crosslinked (meth)acrylate polymer would be difficult to dissolve in the first monomer composition. In many embodiments, the second monomer composition does not contain an aromatic monomer (i.e., a monomer with an aromatic group such as a styrenic monomer or aryl (meth)acrylate).

The second monomer composition often contains 10 to 100 weight percent of a non-acidic high $T_g$ monomer, 0 to 90 weight percent of the alkyl acrylate having a linear or branched alkyl group with at least four carbon atoms and/or of the alkyl methacrylate having a linear or branched group with at least five carbon atoms, 0 to 10 weight percent of a polar monomer that is an acid-containing monomer and/or a hydroxyl-containing monomer, and 0 to 10 weight percent of a vinyl monomer that is not a (meth)acryloyl group. In many embodiments, the only monomers in the second monomer composition are the non-acidic high $T_g$ monomer or the non-acidic high $T_g$ monomer in combination with one or more optional monomers selected from an alkyl acrylate having an alkyl group that is linear or branched with at least four carbon atoms and/or an alkyl methacrylate having an alkyl group that is linear or branched with at least five carbon atoms, and a polar monomer that is an acid-containing monomer and/or a hydroxyl-containing monomer. In such embodiments, the second monomer composition contains 10 to 100 weight percent of a non-acidic high $T_g$ monomer, 0 to 90 weight percent of the alkyl acrylate having a linear or branched alkyl group with at least four carbon atoms and/or of the alkyl methacrylate having a linear or branched alkyl group with at least five carbon atoms, and 0 to 10 weight percent of a polar monomer that is an acid-containing monomer and/or a hydroxyl-containing monomer.

In some specific embodiments, the second monomer composition contains 100 weight percent non-acidic high $T_g$ monomer. The high $T_g$ monomer can be a single monomer or a combination of monomers. In some embodiments, all of the non-acidic high $T_g$ monomer is an alkyl (meth)acrylate having a cyclic alkyl group with 6 to 12 carbon atoms, an alkyl methacrylate having a linear or branched alkyl group with 1 to 4 carbon atoms, or a combination thereof. In other embodiments, the second monomer composition contains at least 80 weight percent of one or both of these high $T_g$ monomers in combination with up to 20 weight percent of other non-acidic high $T_g$ monomers discussed above. For example, the second monomer composition can include two different non-acidic high $T_g$ monomers such as (1) 80 to 99 weight percent of an alkyl (meth)acrylate having a cyclic alkyl group with 6 to 12 carbon atoms, of an alkyl methacrylate having an alkyl group with 1 to 4 carbon atoms, or a combination thereof and (2) 1 to 20 weight percent of another type of non-acidic high $T_g$ monomer.

In some other specific embodiments, the second monomer composition can contain 15 to 85 weight percent of the non-acidic high $T_g$ monomer, 15 to 85 weight percent of the alkyl acrylate having a linear or branched alkyl group with at least four carbon atoms and/or of the alkyl methacrylate having a linear or branched alkyl group with at least five carbon atoms, 0 to 10 weight percent of the polar monomer that is an acid-containing monomer and/or a hydroxyl-containing monomer. In other examples, the second monomer composition can contain 15 to 85 weight percent of the non-acidic high $T_g$ monomer, 15 to 85 weight percent of the alkyl acrylate having a linear or branched alkyl group with at least four carbon atoms and/or of the alkyl methacrylate having a linear or branched alkyl group with at least five carbon atoms, and 0 to 5 weight percent of the polar monomer that is an acid-containing monomer and/or a hydroxyl-containing monomer. In still other examples, the second monomer composition can contain 20 to 80 weight percent of the non-acidic high $T_g$ monomer, 20 to 80 weight percent of the alkyl acrylate having a linear or branched alkyl group with at least four carbon atoms and/or of the alkyl methacrylate having a linear or branched alkyl group with at least five carbon atoms, 0 to 5 weight percent polar monomer that is an acid-containing monomer and/or a hydroxyl-containing monomer. In yet other examples, the second monomer composition can contain 30 to 70 weight percent of the non-acidic high $T_g$ monomer, 30 to 70 weight percent of the alkyl acrylate having an alkyl group with at least four carbon atoms and/or of the alkyl methacrylate having a linear or branched alkyl group with at least five carbon atoms, 0 to 5 weight percent of the polar monomer that is an acid-containing monomer and/or a hydroxyl-containing monomer. The weight percents are based on the total weight of monomers in the second monomer composition.

For any of these specific embodiments that contain optional monomers in the second monomer composition, the non-acidic high $T_g$ monomer can be a mixture of different monomers. If the total amount of high $T_g$ monomer is greater than 20 weight percent of the monomers in the second monomer composition, the high $T_g$ monomer is typically a mixture of a first non-acidic high $T_g$ monomer and a second non-acidic high $T_g$ monomer. The first non-acidic high $T_g$ monomer is selected from an alkyl (meth)acrylate having a cyclic alkyl group with 6 to 12 carbon atoms, an alkyl methacrylate having a linear or branched alkyl group with 1 to 4 carbon atoms, and a mixture thereof. The second non-acidic high $T_g$ monomer is selected from acrylamide, (meth)acrylonitrile, N-alkyl acrylamide having an alkyl group with 1 to 10 carbon atoms, N,N-dialkyl acrylamide having alkyl groups with 1 to 10 carbon atoms, and a mixture thereof.

In addition to the second monomer composition, the polymerizable composition used to form the second (meth)acrylate polymer often contains a chain transfer agent. The chain transfer agent is used to control the molecular weight of the second (meth)acrylate polymer. Examples of useful chain transfer agents include, but are not limited to, carbon tetrabromide, alcohols (e.g., ethanol and isopropanol), thiols (e.g., lauryl mercaptan, butyl mercaptan, ethanethiol, isooctylthioglycolate, 2-ethylhexyl thioglycolate, 2-ethylhexyl mercaptopropionate, ethyleneglycol bisthioglycolate), and mixtures thereof. In many embodiments, the preferred chain transfer agent is iso-octyl thioglycolate (IOTG), carbon tetrabromide, or tert-dodecylmercaptan (TDDM). The amount of the optional chain transfer agent is often in a range of 0 to 5 weight percent based on the total weight of monomers in the second monomer composition. If present, the chain transfer agent is often used in an amount of at least 0.01 weight percent, at least 0.02 weight percent, at least 0.05 weight percent, or at least 0.1 weight percent. The amount can be up to 5 weight percent, up to 3 weight percent, up to 2 weight percent, up to 1 weight percent, or up to 0.5 weight percent.

Other optional components can be added along with the second monomer composition to the polymerizable composition used to form the high second (meth)acrylate polymer. For example, the polymerizable composition can include an inhibitor and/or antioxidant. Suitable inhibitors and/or antioxidants include, but are not limited to, mono-methyl ether of hydroquinone (MEQH) and pentaerythritol tetrakis (3-(3, 5-di-tert-butyl-4-hydroxyphenyl) propionate), which is commercially available from BASF (Florham Park, N.J., USA) under the trade designation IRGANOX 1010.

The polymerizable composition used to form the second (meth)acrylate polymer typically includes a free radical initiator to commence polymerization of the monomers. The free radical initiator can be a photoinitator or a thermal initiator. The free radical initiator is typically present in an amount up to 5 weight percent based on the total weight of the monomers in the second monomer composition. In some embodiments, the amount of free radical initiator is up to 4 weight percent, up to 3 weight percent, up to 2 weight percent, or up to 1 weight percent. The amount of free radical initiator included in the polymerizable composition is typically at least 0.005 weight percent. For example, the polymerizable composition often contains at least 0.01 weight percent, at least 0.02 weight percent, at least 0.05 weight percent, at least 0.1 weight percent, at least 0.2 weight percent, or at least 0.5 weight percent free radical initiator.

Suitable thermal initiators include various azo compound such as those commercially available under the trade designation VAZO from E. I. DuPont de Nemours Co. (Wilmington, Del., USA) including VAZO 67, which is 2,2'-azobis (2-methylbutane nitrile), VAZO 64, which is 2,2'-azobis (isobutyronitrile), VAZO 52, which is (2,2'-azobis(2,4-dimethylpentanenitrile), and VAZO 88, which is 1,1'-azobis (cyclohexanecarbonitrile); various peroxides such as benzoyl peroxide, cyclohexane peroxide, lauroyl peroxide, di-tert-amyl peroxide, tert-butyl peroxy benzoate, di-cumyl peroxide, and peroxides commercially available from Atofina Chemical, Inc. (Philadelphia, Pa., USA) under the trade designation LUPERSOL (e.g., LUPERSOL 101, which is 2,5-bis(tert-butylperoxy)-2,5-dimethylhexane, and LUPERSOL 130, which is 2,5-dimethyl-2,5-di-(tert-butylperoxy)-3-hexyne); various hydroperoxides such as tert-amyl hydroperoxide and tert-butyl hydroperoxide; and mixtures thereof.

In some embodiments, a photoinitiator is used. Some exemplary photoinitiators are benzoin ethers (e.g., benzoin methyl ether or benzoin isopropyl ether) or substituted benzoin ethers (e.g., anisoin methyl ether). Other exemplary photoinitiators are substituted acetophenones such as 2,2-diethoxyacetophenone or 2,2-dimethoxy-2-phenylacetophenone (commercially available under the trade designation IRGACURE 651 from BASF Corp. (Florham Park, N.J., USA) or under the trade designation ESACURE KB-1 from Sartomer (Exton, Pa., USA)). Still other exemplary photoinitiators are substituted alpha-ketols such as 2-methyl-2-hydroxypropiophenone, aromatic sulfonyl chlorides such as 2-naphthalenesulfonyl chloride, and photoactive oximes such as 1-phenyl-1,2-propanedione-2-(O-ethoxycarbonyl) oxime. Other suitable photoinitiators include, for example, 1-hydroxycyclohexyl phenyl ketone (commercially available under the trade designation IRGACURE 184), bis(2,4,6-trimethylbenzoyl)phenylphosphineoxide (commercially available under the trade designation IRGACURE 819), 1-[4-(2-hydroxyethoxy)phenyl]-2-hydroxy-2-methyl-1-propane-1-one (commercially available under the trade designation IRGACURE 2959), 2-benzyl-2-dimethylamino-1-(4-morpholinophenyl)butanone (commercially available under the trade designation IRGACURE 369), 2-methyl-1-[4-(methylthio)phenyl]-2-morpholinopropan-1-one (commercially available under the trade designation IRGACURE 907), and 2-hydroxy-2-methyl-1-phenyl propan-1-one (commercially available under the trade designation DAROCUR 1173 from Ciba Specialty Chemicals Corp. (Tarrytown, N.Y., USA)).

Additionally, an organic solvent can be added if desired to control the viscosity of the polymerizable composition used to form the second (meth)acrylate polymer. The amount of organic solvent, if any, is typically determined by the polymerization method. In some solvent-based polymerization methods, the polymerizable composition can contain up to 70 weight percent organic solvent. For adiabatic polymerization methods, however, the amount of organic solvent is typically no greater than 10 weight percent, no greater than 8 weight percent, no greater than 5 weight percent, no greater than 3 weight percent, or no greater than 1 weight percent of the polymerizable composition. Any organic solvent used in the polymerizable composition is typically removed at the completion of the polymerization reaction. Suitable organic solvents include, but are not limited to, methanol, tetrahydrofuran, ethanol, isopropanol, heptane, acetone, methyl ethyl ketone, methyl acetate, ethyl acetate, toluene, xylene, and ethylene glycol alkyl ether. Those solvents can be used alone or as mixtures thereof. In many embodiments (such in some adiabatic polymerization processes), the polymerization occurs with little or no organic solvent present.

The monomers used to form the second (meth)acrylate polymer can be polymerized using any suitable method such as, for example, solution (i.e., with a solvent) polymerization, dispersion polymerization, suspension polymerization, and solventless polymerization (for example, bulk polymerization with either UV or thermal initiator). The polymerization can occur in a single step or in multiple steps. That is, all or a portion of the polymerizable composition may be charged into a suitable reaction vessel and polymerized. If multiple steps are used, an initial charge of monomers and initiator are added to the reactor. After polymerization of the initial charge, another portion of any remaining monomers and/or initiator are added. Multiple polymerization steps can help narrow the polydispersity of the polymerized product (e.g., the amount of low molecular weight chains can be reduced), can help minimize or control the heat of reaction, and can allow for adjustment of the type and amount of monomer available during polymerization.

In many embodiments, the second (meth)acrylate polymer is not formed using emulsion or dispersion polymerization methods. Rather, the second (meth)acrylate polymer is prepared using a solventless or solvent bulk polymerization method. Either a thermal initiator or a photoinitiator can be used. In some embodiments, polymerization occurs using an adiabatic process as described, for example, in U.S. Pat. No. 5,986,011 (Ellis et al.) and U.S. Pat. No. 5,637,646 (Ellis). A thermal initiator is used with this process.

The weight average molecular weight of the second (meth)acrylate polymer is typically at least 3,000 grams/mole. If the weight average molecular weight is lower, the resulting pressure-sensitive adhesive may have an unacceptably low cohesive strength. The second (meth)acrylate polymer often has a weight average molecular weight of at least 5,000 grams/mole, at least 10,000 grams/mole, or at least 20,000 grams/mole. The weight average molecular weight can be up to 150,000 grams/mole. If the molecular weight is higher, the second (meth)acrylate polymer might not dissolve in the first monomer composition of the emulsion composition. If not dissolved in the first monomer composition, the second (meth)acrylate polymer can undesirably be present in separate droplets from the first monomer composition within the emulsion composition. The weight average molecular weight is often up to 120,000 grams/mole, up to 100,000 grams/mole, up to 80,000 grams/mole, up to 60,000 grams/mole, or up to 50,000 grams/mole. For example, the weight average molecular weight can be in a range of 3,000 to 150,000 grams/mole, in a range of 3,000 to 100,000 grams/mole, in a range of 3,000 to 50,000 grams/mole, in a range of 5,000 to 100,000, in a range of 5,000 to 80,000 grams/mole, or in a range of 5,000 to 50,000 grams/mole.

The $T_g$ of the second (meth)acrylate polymer is typically greater than $-50°$ C. For example, the $T_g$ is greater than $-45°$ C. or greater than $-40°$ C. The $T_g$ of the second (meth)acrylate polymer can be up to that of a homopolymer formed from the non-acidic high $T_g$ monomer. In many embodiments, the $T_g$ of the second (meth)acrylate polymer can be up to $100°$ C. or higher, up to $80°$ C., up to $70°$ C., or up to $60°$ C. The $T_g$ of the second (meth)acrylate polymer is often in a range of $-45°$ C. to greater than $100°$ C., in a range of $-30°$ C. to $100°$ C., or in a range of $-20°$ C. to $80°$ C.

The second (meth)acrylate polymer is added to the emulsion composition. That is, this polymeric material is prepared prior to combination with the other components of the emulsion composition. The second (meth)acrylate polymer typically does not undergo further free radical polymerization within the emulsion composition or with other components of the emulsion composition. The second (meth)acrylate can, however, undergo a crosslinking reaction within the emulsion composition.

The second (meth)acrylate polymer is usually added to the emulsion composition after being dissolved in the first monomer composition. That is, a solution containing the second (meth)acrylate polymer and the first monomer composition are added together to the first phase of the emulsion. The solution is typically added under conditions of high shear mixing to form droplets suspended within the first phase. In some embodiments, the second (meth)acrylate polymer is initially dissolved in a portion of the first monomer composition and then the resulting polymer solution is then mixed with the remaining monomers of the first monomer composition.

The amount of second (meth)acrylate polymer added to the emulsion composition is typically at least 0.5 weight percent or at least 1 weight percent. If a lower amount of the second (meth)acrylate polymer is added, the stability of the emulsion composition may be poor. That is, it can be difficult to form and maintain droplets in the emulsion composition. In some embodiments, the emulsion composition contains at least 2 weight percent, at least 3 weight percent, or at least 5 weight percent of the second (meth) acrylate polymer. The amount of the second (meth)acrylate polymer added is typically up to 15 weight percent. If a higher amount of the second (meth)acrylate polymer is added, the polymerization of the first monomer composition within the droplets may be undesirably slow. Additionally, the polymeric material formed from the first monomer composition may have an undesirably low molecular weight and the resulting pressure-sensitive adhesive may have an undesirably low cohesive strength. In some embodiments, the emulsion composition contains up to 12 weight percent, up to 10 weight percent, or up to 8 weight percent of the second (meth)acrylate polymer. The weight percents are based on a total weight of the first monomer composition in the emulsion composition (i.e., the total weight of monomers in the first monomer composition).

The emulsion composition contains both the first monomer composition and the second (meth)acrylate polymer. More specifically, the emulsion composition often contains 0.5 to 15 weight percent of the second (meth)acrylate polymer and 85 to 99.5 weight percent first monomer composition based on the total weight of the second (meth) acrylate polymer plus the weight of monomers in the first monomer composition. This is the total polymerized and polymerizable material in the emulsion composition. Most of this polymerized and polymerizable material is present within the droplets of the emulsion (e.g., some of the acidic monomers may be dissolved in the first phase). In some examples, the emulsion composition can contain 1 to 15 weight percent of the second (meth)acrylate polymer and 85 to 99 weight percent of the first monomer composition, 2 to 12 weight percent of the second (meth)acrylate polymer and 88 to 98 weight percent of the first monomer composition, 2 to 10 weight percent of the second (meth)acrylate polymer and 90 to 98 weight percent of the first monomer composition, or 2 to 8 weight percent of the second (meth)acrylate polymer and 92 to 98 weight percent of the first monomer composition based on the total weight of the second (meth) acrylate polymer plus the weight of monomers in the first monomer composition.

Other optional reactants can be included in the emulsion composition. For example, in some embodiments, a crosslinker is added that can react with multiple carboxylic acid groups (—COOH). The carboxylic acid groups can be on the second (meth)acrylate polymer, on the polymeric material formed from the first monomer composition, or on a combination of both polymeric materials. The use of the optional crosslinkers may increase the shear strength of the resulting pressure-sensitive adhesive.

Suitable crosslinkers capable of reacting with multiple carboxylic acid groups include, but are not limited to, polyoxazolines such as those commercially available under the trade designation EPOCROS from Nippon Shokubai Co., LTD (Japan), polyaziridines (e.g., trimehtylolpropane tris(2-methyl-laziridine) propionate from PolyAziridine LCC (Medford, N.J., USA)), polyamines, or the like. Other suitable crosslinkers include metal salts that can complex with multiple carboxylic acid groups. Suitable metals include, for example, zinc salts. If used, the optional crosslinker is often added in an amount equal to at least 0.01 weight percent based on the total weight of monomers in the first monomer composition. For example, the emulsion can contain at least 0.05 weight percent, at least 0.1 weight percent, or at least 0.5 weight percent of the crosslinker. The amount of the optional crosslinker is often up to 3 weight percent based on the total weight of monomers in the first monomer composition. For example, the emulsion composition can contain up to 2.5 weight percent, up to 2 weight percent, up to 1.5 weight percent, or up to 1 weight percent of the optional crosslinker.

In many embodiments, an optional neutralizing agent is added to the emulsion composition. The neutralizing agent can be added, for example, to improve the reactivity of the crosslinker, to improve the stability of the resulting latex composition, or the like. Suitable neutralizing agents are often strong or weak bases such as, for example, ammonium hydroxide, ammonia, sodium acetate, potassium acetate, sodium hydroxide, potassium hydroxide, and lithium hydroxide. The neutralizing agent is often added to increase the pH of the emulsion composition to at least 4.0, at least 4.5, at least 5.0, at least 5.5, at least 6.0, at least 6.5, or at least 7.0.

The emulsion composition typically further includes an initiator. While either a water soluble or oil soluble initiator can be used, the initiator is typically selected to be soluble in water. If the initiator is oil soluble, it is typically added to the mixture of monomers of the first monomer composition and the second (meth)acrylate polymer before this mixture is combined with the first phase of the emulsion composition. If the initiator is water soluble, it is often added after formation of the droplets within the first phase of the emulsion composition. If a reducing agent is used, it is usually water soluble and is added to the first phase.

Examples of water soluble initiators include, but are not limited to, hydrogen peroxide and various persulfate salts such as sodium persulfate, potassium persulfate, and ammonium persulfate. Optional reducing agents can be added to lower the temperature needed for initiation of the polymerization reaction. Suitable reducing agents include, but are not limited to, ascorbic acid, bisulfite salts (e.g., sodium bisulfite, potassium bisulfite, and ammonium bisulfite), and sodium formaldehyde sulfoxylate. The amount of initiator and optional reducing agent can each be up to 1 weight percent based on the weight of monomers in the first monomer composition. For example, the amounts can be up to 0.8 weight percent, up to 0.5 weight percent, up to 0.3 weight percent, or up to 0.2 weight percent based on a total weight of monomers in the first monomer composition. The amount of initiator and optional reducing agent each can be at least 0.01 weight percent, at least 0.05 weight percent, or at least 0.1 weight percent based on the total weight of monomers in the first monomer composition.

Examples of oil soluble initiators include, but are not limited to, azo compounds or peroxides such as those mentioned above for the formation of the second (meth) acrylate polymer. If such initiators are used, they are used in the same amount as described above for water soluble initiators.

In many emulsion compositions, a chain transfer agent is not used. As described above, however, a chain transfer agent can be used (and usually is used) in the formation of the second (meth)acrylate polymer.

An optional tackifier can be included in the emulsion composition, if desired. If such an optional tackifier is added to the emulsion composition, it is typically a C9-based hydrocarbon tackifier. These tackifiers are derived mainly from C9 monomers with some other monomers present such as a mixture of vinyl toluenes, dicyclopenadiene, indene, methylstyrene, styrene, and methylindenes. The C9-based hydrocarbon tackifiers are commercially available from Eastman Chemical Company under the trade designation PICCO, KRISTALEX, PLASTOLYN, PICCOTAC, and ENDEX, from Cray Valley (Exton, Pa., USA) under the trade designations NORSOLENE, from Ruetgers N.V. (Belgium) under the trade designation NOVAREZ, and from Kolon Industries, Inc. (South Korea) under the trade designation HIKOTAC. These resins can be partially or fully hydrogenated. Prior to hydrogenation, the C9-based hydrocarbon resins are often about 40 percent aromatic as measured by proton Nuclear Magnetic Resonance. Hydrogenated C9-based hydrocarbon resins are commercially available, for example, from Eastman Chemical under the trade designations REGALITE and REGALREZ that are 50 to 100 percent (e.g., 50 percent, 70 percent, 90 percent, and 100 percent) hydrogenated. The partially hydrogenated resins typically have some aromatic rings.

If present, the optional tackifier in the emulsion composition is often present in an amount in a range of 1 to 40 weight percent based on the total weight of the second (meth)acrylate copolymer plus the weight of monomers in the first monomer composition. In some embodiments, the amount of tackifier is at least 5 weight percent, at least 10 weight percent, or at least 15 weight percent and can be up to 35 weight percent, up to 30 weight percent, up to 25 weight percent, or up to 20 weight percent.

The emulsion composition can be prepared by any suitable process that results in the formation of droplets containing the second (meth)acrylate polymer dissolved in monomers of the first monomer composition. In many embodiments, the second (meth)acrylate polymer is initially mixed with monomers included in the first monomer composition. The monomers are often used in their neat form without the addition of any solvent. Once the second (meth)acrylate polymer has dissolved, the mixture is combined with water or with water and other components of the emulsion composition using high shear mixing. In some embodiments, the polymerizable surfactant and neutralizing agent can be dissolved in (or combined with) the water prior to mixing.

With high shear mixing, droplets form within the first phase (i.e., aqueous phase). Prior to any polymerization of the first monomer composition, the droplets contain a mixture of i) the second (meth)acrylate polymer and ii) at least 85 weight percent of the first monomer composition, wherein the second (meth)acrylate polymer is dissolved in the first monomer composition within the droplets.

Typically, the droplets include at least 92 weight percent, at least 95 weight percent, at least 97 weight percent, at least 98 weight percent, or at least 99 weight percent of the monomers in the first monomer composition. The alkyl (meth)acrylate is likely to be predominately within the droplets while the acidic monomers may be distributed partially within the droplets and partially within the aqueous phase. The polymerizable surfactant is likely to be at the interface between the droplets and the first phase or dissolved in first phase. Most of the polymerizable surfactant is likely to be at the interface. In many embodiments, any initiator, and/or reducing agent, and/or neutralizing agents included in the emulsion composition are likely to be dissolved in the first phase.

The droplets suspended in the first phase typically have an average diameter up to about 2000 nanometers, up to 1500 nanometers, up to 1000 nanometers, up to 900 nanometers, up to 800 nanometers, up to 700 nanometers, up to 600 nanometers, or up to 500 nanometers. The average diameter is typically at least 100 nanometers, at least 200 nanometers, at least 300 nanometers, or at least 400 nanometers. The average size can be determined using dynamic light scattering methods. In some embodiments, the average droplet size is in a range of 100 to 2000 nanometers, in a range of 200 to 1000 nanometers, in a range of 300 to 1000 nanometers, in a range of 200 to 800 nanometers, or in a range of 400 to 700 nanometers.

In many embodiments, the emulsion composition is considered to be a mini-emulsion. As used herein, the term "mini-emulsion" refers to an emulsion method that uses high shear to make droplets having a diameter no greater than 1 micrometer. Polymerization occurs within the droplets to form polymeric latex particles. Polymerization is limited to that which occurs within the droplets.

The emulsion composition is typically concurrently agitated and at room temperature (e.g., about 20° C. to about 25° C.) or at a temperature above room temperature to polymerize the first monomer within the droplets. The temperature is often at least 30° C., at least 40° C., or at least 50° C. The temperature can be up to the boiling temperature of the emulsion composition (e.g., about 100° C.). In some embodiments, the temperature can be up to 80° C., up to 70° C., or up to 60° C. Any heat generated during polymerization is rapidly moderated by the effect of the heat capacity of the first phase. The reaction time can be any length of time needed to complete the polymerization reaction. In some embodiments, the reaction time can be at least 1 hour, at least 2 hours, at least 3 hours, or at least 4 hours. The reaction time is up to 24 hours or longer, up to 16 hours, or up to 8 hours. The reactor is often purged with an inert gas such as nitrogen.

The polymerized product of the emulsion composition is a latex composition. That is, the latex composition contains water and polymeric particles that are a polymerized product of the emulsion composition as described above. The terms "latex" and "latex composition" may be used interchangeably. The terms "polymeric particle" and "latex particles" and "polymeric latex particles" may be used interchangeably. Both i) the second (meth)acrylate polymer plus ii) the polymerized product of the first monomer composition (the first (meth)acrylate polymer) are present within the same latex particles. The latex composition contains latex particles having an average size comparable to the average size of the droplets within the emulsion composition prior to polymerization. More particularly, the average particle size of the latex particles is roughly equal to or slightly larger than the average droplet size within the emulsion composition due to density differences.

The latex particles are typically suspended (e.g., dispersed) in the water phase. Preferably, the latex particles are not coagulated together. The latex particles include both the second (meth)acrylate polymer and the first (meth)acrylate polymer. The molecular weight of the first (meth)acrylate polymer is typically higher than the molecular weight of polymeric materials of the same overall chemical composition formed using other processes. More specifically, the molecular weight of the first (meth)acrylate polymer formed by emulsion polymerization can be close to 1 million Daltons.

In contrast to the emulsion method used to form the first (meth)acrylate polymer, a typical molecular weight of polymers formed from the same monomers using solution polymerization or bulk polymerization methods is often less than 500,000 Daltons. With both solution polymerization and bulk polymerization methods, the molecular weight is usually controlled by the initiator concentration. That is, higher initiator concentrations tend to produce lower molecular weight polymers. Therefore, in order to produce high molecular weight polymers using solution polymerization or bulk polymerization methods, extremely low initiator concentrations are required. However, if extremely low initiator concentrations are used, the polymerization time may be unacceptably long. Such processes may be economically impractical to prepare high molecular weight polymeric materials. The high molecular weight polymeric materials, however, are often desirable for some adhesive applications such as where high shear strength is necessary.

With emulsion polymerization methods, the molecular weight of the polymeric material (e.g., the molecular weight of the first (meth)acrylate polymer) can be controlled by both initiator concentration and the number of particles (i.e., number of droplets in the emulsion). Higher initiator concentrations often result in lower molecular weights and faster reaction times. Higher particle numbers, however, tend to favor higher molecular weights and faster reaction times.

Due to the high molecular weight of the polymeric materials formed from emulsion compositions, crosslinking structures can often form more easily compared to polymeric materials formed using solution polymerization and bulk polymerization methods without additional crosslinkers. Two possible types of crosslinking can occur in the polymeric materials formed by emulsion polymerization: 1) physical entanglement and 2) chemical crosslinking due to the chain transfer reactions to a polymeric chain. Physical entanglement can be enhanced with longer polymeric chains resulting from the increased average molecular weight. Chain transfer reactions can form crosslinking structures for long polymeric chains.

The latex particles typically have a single glass transition temperature as determined using a Differential Scanning calorimeter. More specifically, there is a single peak in the plot of reversible heat flow versus temperature for the dry polymeric material during the second heating cycle using Modulated Differential Scanning calorimetry. The $T_g$ is typically no greater than 0° C., no greater than –10° C., or no greater than –20° C.

The latex composition can be combined with an optional tackifier. The addition of a tackifer can be used to increase adhesion. Any suitable tackifier can be used such as rosin acids and their derivatives (e.g., rosin esters); terpene resins such as polyterpenes (e.g., alpha pinene-based resins, beta pinene-based resins, and limonene-based resins, and aromatic-modified polyterpene resins (e.g., phenol modified polyterpene resins)); coumarone-indene resins; and petroleum-based hydrocarbon resins such as C5-based hydrocarbon resins, C9-based hydrocarbon resins, C5/C9-based hydrocarbon resins, and dicyclopentadiene-based resins. These tackifying resins, if added, can be hydrogenated to lower their color contribution to the pressure-sensitive adhesive composition. Combinations of various tackifiers can be used, if desired.

In many embodiments, the tackifier is a rosin ester or includes a rosin ester. Tackifiers that are rosin esters are the reaction products of various rosin acids and alcohols. These include, but are not limited to, methyl esters of rosin acids, triethylene glycol esters of rosin acids, glycerol esters of rosin acids, and pentaertythritol esters of rosin acids. These rosin esters can be hydrogenated partially or fully to improve stability and reduce their color contribution to the pressure-sensitive adhesive composition. The rosin resin tackifiers are commercially available, for example, from Eastman Chemical Company (Kingsport, Tenn., USA) under the trade designations PERMALYN, STAYBELITE, and FORAL as well as from Newport Industries (London, England) under the trade designations NUROZ and NUTAC. A fully hydrogenated rosin resin is commercially available, for example, from Eastman Chemical Company under the trade designation FORAL AX-E. A partially hydrogenated rosin resin is commercially available, for example, from Eastman Chemical Company under the trade designation STAYBELITE-E.

Often, it is desirable to use a tackifier that can be dispersed in water. Water dispersions of rosin esters are available under the trade designation SNOWTACK from Lawter, Inc. (Chicago, Ill., USA). Other suitable water dispersed tackifiers are commercially available under the trade designation TACOLYN from Eastman Chemical Company that include, for example, rosin ester resin dispersions, hydrogenated rosin ester resin dispersions, aliphatic hydrocarbon resin dispersions, and aromatic modified hydrocarbon resin dispersion.

If present, the optional tackifier in the latex composition is often present in an amount in a range of 1 to 40 weight percent based on the total weight of the polymeric latex particles. In some embodiments, the amount of tackifier is at least 5 weight percent, or at least 10 weight percent and can be up to 35 weight percent, up to 30 weight percent, up to 25 weight percent, or up to 20 weight percent.

Other optional components that can be added to the latex composition are thickeners. Example thickeners are typically aqueous polymer solutions such as those available under the trade designation PARAGUM from Royal Coatings and Specialty Polymers. If added, the optional thickeners can be used in amounts up to 5 weight percent based on the total weight of the latex composition (water and polymeric latex particles). For example, the thickener can be used in an amount up to 4 weight percent, up to 3 weight percent, up to 2 weight percent, or up to 1 weight percent. In some embodiments, the thickener is in a range of 0 to 5 weight percent, 0.1 to 5 weight percent, 0.1 to 2 weight percent, 0.1 to 1 weight percent, 0.2 to 0.8 weight percent, or 0.4 to 0.6 weight percent.

The latex composition typically is dried to form a pressure-sensitive adhesive. The compositions are typically dried to remove at least 90 weight percent of the water. For example, at least 95 weight percent, at least 97 weight percent, at least 98 weight percent, or at least 99 weight percent of the water is removed. The water content of the dried pressure-sensitive adhesive many increase or decrease depending on the environmental humidity. In some embodiments, the latex composition is coated on a substrate such as a backing layer or release liner prior to drying. Drying typically occurs at temperatures above room temperature but not at a temperature that would distort or degrade the substrate and/or the pressure-sensitive adhesive layer. In some embodiments, the drying occurs at temperatures in a range of about 40° C. to about 120° C. and for a time sufficient to lower the water content to the desired level.

The pressure-sensitive adhesive layer can have any desired thickness. In many embodiments, the adhesive layer has a thickness no greater than 20 mils (500 micrometers), no greater than 10 mils (250 micrometers), no greater than 5 mils (125 micrometers), no greater than 4 mils (100 micrometers), no greater than 3 mils (75 micrometers), or no greater than 2 mils (50 micrometers). The thickness is often at least 0.5 mils (12.5 micrometers) or at least 1 mil (25 micrometers). For example, the thickness of the adhesive layer can be in the range of 0.5 mils (2.5 micrometers) to 20 mils (500 micrometers), in the range of 0.5 mils (5 micrometers) to 10 mils (250 micrometers), in the range of 0.5 mils (12.5 micrometers) to 5 mils (125 micrometers), in the range of 1 mil (25 micrometers) to 3 mils (75 micrometers), or in the range of 1 mil (25 micrometers) to 2 mils (50 micrometers).

Various types of articles can be prepared that include a substrate and a pressure-sensitive adhesive layer positioned adjacent to a major surface of the substrate. Any suitable substrate can be used in the article and the substrate is often selected depending on the particular application. For example, the substrate can be flexible or inflexible and can be formed from a polymeric material, glass or ceramic material, metal or metal alloy, or combination thereof. Some substrates are polymeric materials such as those prepared, for example, from polyolefins (e.g., polyethylene, polypropylene, or copolymers thereof), polyurethanes, polyvinyl acetates, polyvinyl chlorides, polyesters (polyethylene terephthalate or polyethylene naphthalate), polycarbonates, polyacrylates such as polymethyl(meth)acrylates (PMMA), ethylene-vinyl acetate copolymers, neoprenes, and cellulosic materials (e.g., cellulose acetate, cellulose triacetate, and ethyl cellulose). The substrate can be in the form of foils or films, nonwoven materials (e.g., paper, cloth, nonwoven scrims), foams, and the like. For some substrates, it may be desirable to treat the surface of the substrate to improve adhesion to the pressure-sensitive adhesive layer. Such treatments include, for example, application of primer layers, surface modification layer (e.g., corona treatment or surface abrasion), or both.

In some embodiments, the substrate is a release liner. Release liners typically have low affinity for the pressure-sensitive adhesive layer. Exemplary release liners can be prepared from paper (e.g., Kraft paper) or other types of polymeric material. Some release liners are coated with an outer layer of a release agent such as a silicone-containing material or a fluorocarbon-containing material.

Some articles are adhesive tapes. The adhesive tapes can be single-sided adhesive tapes with the pressure-sensitive adhesive on a single side of the backing layer or can be double-sided adhesive tape with a pressure-sensitive adhesive layer on both major surfaces of the backing layer. The backing layer is often a film or foam. Each pressure-sensitive adhesive layer may be positioned, if desired, between the backing layer and a release layer.

Any suitable backing layer can be used. In some embodiments, the backing layer is an oriented polyolefin film. For example, the oriented polyolefin film can prepared as described in U.S. Pat. No. 6,638,637 (Hager et al.). Such backings layers often include multiple layers of polyolefins with at least two different melting points and that are biaxially oriented. In another example, the oriented polyolefin film can be prepared as described in U.S. Pat. No. 6,451,425 (Kozulla et al.). Such backings often include an isotactic polypropylene that is blended or mixed with at least one second polyolefin such as polyethylene, polybutylene, or syndiotactic polypropylene. These backings are typically biaxially oriented.

For adhesive tapes with a single pressure-sensitive adhesive layer, the backing layer often has a first surface that has been treated (i.e., primed) to improve adhesion to the pressure-sensitive adhesive layer. The backing layer has a second surface opposite the first surface that has a low adhesion to the pressure-sensitive adhesive layer. Such an adhesive tape can be formed into a roll. In some embodiments, the adhesive tapes are packaging tapes.

Other articles are transfer tapes in which a pressure-sensitive adhesive layer is positioned adjacent to a release liner. The transfer tape can be used to transfer the pressure-sensitive adhesive layer to another substrate or surface. Any suitable release liner can be used. In many embodiments, the release liner has a release layer coating adjacent to a substrate. Suitable substrates include, but are not limited to, paper such as poly-coated Kraft paper and super-calendered or glassine Kraft paper; cloth; nonwoven web; metal including metal foil; polyesters such as poly(alkylene terephthalate) such as poly(ethylene terephthalate), poly(alkylene naphthalate) such as poly(ethylene naphthalate); polycarbonate; polyolefins such as polypropylene, polyethylene, and copolymers thereof; polyamide; cellulosic materials such as cellulose acetate or ethyl cellulose; and combinations thereof.

In some exemplary embodiments, the release liners have a release coating containing a polymerized product of a vinyl-silicone copolymer as described in U.S. Pat. No. 5,032,460 (Kantner et al.). In other exemplary embodiments, the release liner has a release coating containing a polymerized product of a (meth)acrylate-functionalized siloxane as described in U.S. Patent Application Publication 2013/059105 (Wright et al.). Such release coatings can be prepared by applying a coating of a polymerizable composition containing the (meth)acrylate-functionalized polysiloxane to a surface of a substrate and then irradiating the coating with ultraviolet radiation. The ultraviolet radiation is often provided by short wavelength polychromatic ultraviolet light source having at least one peak with intensity at a wavelength in the range of about 160 to about 240 nanometers. Suitable short wavelength polychromatic ultraviolet light sources include, for example, low pressure mercury vapor lamps, low pressure mercury amalgam lamps, pulsed Xenon lamps, and glow discharge from a polychromic plasma emission source. The coatings applied to the substrate can be free or substantially free (e.g., less than 0.1 weight percent, less than 0.01 weight percent, or less than 0.001 weight percent) of a photoinitiator based on the total weight of the coatings.

The pressure-sensitive adhesive layers often have both high peel adhesion and high shear strength (i.e., cohesion). As such, adhesive tapes formed by applying a pressure-sensitive adhesive layer to a backing can be used for diverse applications. In some embodiments, the adhesive tape can be used as a packaging tape.

Embodiment 1 is an emulsion composition. The emulsion composition contains a) water, b) a polymerizable surfactant having an unsaturated group that can undergo free radical polymerization, c) a first monomer composition, and d) a second (meth)acrylate polymer. The first monomer composition includes 1) an alkyl (meth)acrylate having an alkyl group with at least at least six carbon atoms, 2) a first acidic monomer having a glass transition temperature equal to at least 100° C. when measured as a homopolymer, and 3) a second acidic monomer having a glass transition temperature no greater than 50° C. when measured as a homopolymer. The second (meth)acrylate polymer is present in an amount of 0.5 to 15 weight percent based on a total weight of monomers in the first monomer composition. The second (meth)acrylate polymer has a weight average molecular weight in a range of 3,000 to 1,500,000 Daltons and a glass transition temperature greater than −50° C. The second (meth)acrylate polymer is formed from a second monomer composition containing at least 10 weight percent of a non-acidic high $T_g$ monomer based on a total weight of monomers in the second monomer composition. The non-acidic high $T_g$ monomer has a glass transition temperature equal to at least 80° C. when measured as a homopolymer. The emulsion contains a first phase that includes the water and a second phase dispersed as droplets within the first phase. The droplets contain a mixture of i) at least 85 weight percent of the first monomer composition and ii) the second (meth)acrylate polymer. The second (meth)acrylate polymer is not miscible with the first phase and is dissolved in the first monomer composition within the droplets.

Embodiment 2 is the emulsion composition of embodiment 1, wherein the emulsion composition contains at least 30 weight percent water based on a total weight of the emulsion composition.

Embodiment 3 is the emulsion composition of any one of embodiments 1 or 2, wherein the emulsion composition contains up to 90 weight percent water based on the total weight of the emulsion composition.

Embodiment 4 is the emulsion composition of any one of embodiments 1 to 3, wherein the polymerizable surfactant is a propenyl polyoxyethylene alkylphenyl compound or propenyl polyoxyethylene alkylphenyl ether ammonium sulfate compound.

Embodiment 5 is the emulsion composition of any one of embodiments 1 to 3, wherein the polymerizable surfactant is sodium dodecylallyl sulfosuccinate or a phosphate ester.

Embodiment 6 is the emulsion composition of any one of embodiments 1 to 5, wherein the emulsion composition contains at least 0.5 weight percent polymerizable surfactant based on the total weight of monomers in the first monomer composition.

Embodiment 7 is the emulsion composition of any one of embodiments 1 to 6, wherein the emulsion composition contains up to 2 weight percent polymerizable surfactant based on the total weight of monomers in the first monomers composition.

Embodiment 8 is the emulsion composition of any one of embodiments 1 to 7, wherein the first monomer composition comprises at least 65 weight percent of the alkyl (meth) acrylate having the alkyl group with at least six carbon atoms.

Embodiment 9 is the emulsion composition of any one of embodiments 1 to 8, wherein the first monomer composition comprises up to 98.5 weight percent of the alkyl (meth) acrylate having the alkyl group with at least six carbon atoms.

Embodiment 10 is the emulsion composition of any one of embodiments 1 to 9, wherein the first acidic monomer in the first monomer composition comprises acrylic acid, methacrylic acid, itaconic acid, maleic anhydride, maleic acid, or a mixture thereof and wherein the second acidic monomer in the first monomer composition comprises carboxyethyl acrylate, mono-2-acryloyloxyethyl succinate, or a mixture thereof.

Embodiment 11 is the emulsion composition of any one of embodiments 1 to 10, wherein the first acidic monomer in the first monomer composition is acrylic acid, methacrylic acid, or a mixture thereof.

Embodiment 12 is the emulsion composition of any one of embodiments 1 to 11, wherein the second acidic monomer in the first monomer composition is carboxyethyl acrylate, mono-2-acryloyloxyethyl succinate, or a combination thereof.

Embodiment 13 is the emulsion composition of any one of embodiments 1 to 12, wherein the first monomer composition contains 65 to 98.5 weight percent of the alkyl (meth)acrylate having at least six carbon atoms, 0 to 20 weight percent of an alkyl (meth)acrylate having an alkyl group with one to five carbon atoms, 0.5 to 5 weight percent of the first acidic monomer, and 1 to 10 weight percent of the second acidic monomer based on the total weight of monomers in the first monomer composition.

Embodiment 14 is the emulsion composition of any one of embodiments 1 to 13, wherein the first monomer composition contains 85 to 98.5 weight percent of the alkyl (meth)acrylate having at least six carbon atoms, 0.5 to 5 weight percent of the first acidic monomer, and 1 to 10 weight percent of the second acidic monomer based on the total weight of monomers in the first monomer composition.

Embodiment 15 is the emulsion composition of any one of embodiments 1 to 14, wherein the second monomer composition is not identical to the first monomer composition.

Embodiment 16 is the emulsion composition of any one of embodiments 1 to 15, wherein the second (meth)acrylate polymer has a glass transition temperature greater than −40° C.

Embodiment 17 is the emulsion composition of any one of embodiments 1 to 16, wherein the non-acidic high $T_g$ monomer in the second monomer composition is an alkyl (meth)acrylate having a cyclic alkyl group with 6 to 12 carbon atoms.

Embodiment 18 is the emulsion composition of any one of embodiments 1 to 17, wherein the non-acidic high $T_g$ monomer in the second monomer composition is isobornyl (meth)acrylate, 3,3,5-trimethylcyclohexyl methacrylate, cyclohexyl methacrylate, 3,5-dimethyladamantyl acrylate, 4-tert-butylcyclohexyl methacrylate, or a mixture thereof.

Embodiment 19 is the emulsion composition of embodiment 17 or 18, wherein the second monomer composition comprises 10 to 100 weight percent of the alkyl (meth) acrylate having a cyclic alkyl group with 6 to 12 carbon atoms.

Embodiment 20 is the emulsion composition of any one of embodiments 1 to 16, wherein the non-acidic high $T_g$ monomer in the second monomer composition is an alkyl methacrylate having a linear or branched alkyl group with 1 to 4 carbon atoms.

Embodiment 21 is the emulsion composition of embodiment 20, wherein the second monomer composition comprises up to 20 weight percent of the alkyl methacrylate having the linear or branched alkyl group with 1 to 4 carbon atoms.

Embodiment 22 is the emulsion composition of any one of embodiments 1 to 16, wherein the non-acidic high $T_g$ monomer in the second monomer composition is acrylamide, (meth)acrylonitrile, N-alkyl acrylamide, or N,N-dialkyl acrylamide.

Embodiment 23 is the emulsion composition of embodiment 22, wherein the second monomer composition comprises up to 20 weight percent of the acrylamide, (meth) acrylonitrile, N-alkyl acrylamide, or N,N-dialkyl acrylamide.

Embodiment 24 is the emulsion composition of any one of embodiments 1 to 23, wherein the second monomer composition further comprises an alkyl acrylate with a linear or branched alkyl group with at least 4 carbon atoms and/or an alkyl methacrylate with a linear or branched alkyl group with at least 5 carbon atoms.

Embodiment 25 is the emulsion composition of any one of embodiments 1 to 24, wherein the second monomer composition further comprises a polar monomer.

Embodiment 26 is the emulsion composition of embodiment 25, wherein the polar monomer is an acid-containing monomer, a hydroxyl-containing monomer, or a mixture thereof.

Embodiment 27 is the emulsion composition of any one of embodiments 1 to 26, wherein the second monomer composition comprises 10 to 100 weight percent of the non-acidic high $T_g$ monomer, 0 to 90 weight percent of an alkyl acrylate having a linear or branched alkyl group with at least 4 carbon atoms and/or of an alkyl methacrylate having a linear or branched alkyl group with at least 5 carbon atoms, and 0 to 10 weight percent of a polar monomer that is an acid-containing monomer, a hydroxyl-containing monomer, or a mixture thereof. Each amount is based on a total weight of monomers in the second monomer composition.

Embodiment 28 is the emulsion composition of embodiment 27, wherein the non-acidic high $T_g$ monomer comprises a first non-acidic high $T_g$ monomer that is an alkyl (meth)acrylate having a cyclic alkyl group with 6 to 12 carbon atoms.

Embodiment 29 is the emulsion composition of embodiment 27, wherein the non-acidic high $T_g$ monomer in the second monomer composition comprises an alkyl methacrylate having a linear or branched alkyl group with 1 to 4 carbon atoms, acrylamide, (meth)acrylonitrile, N-alkyl acrylamide having an alkyl group with 1 to 10 carbon atoms, N,N-dialkyl acrylamide having alkyl groups with 1 to 10 carbon atoms, or a combination thereof.

Embodiment 30 is the emulsion composition of any one of embodiments 1 to 29, wherein the non-acidic high $T_g$ monomer comprises 1) a first high $T_g$ monomer comprising an alkyl (meth)acrylate having a cyclic alkyl group with 6 to 12 carbon atoms, an alkyl methacrylate having a linear or branched alkyl group with 1 to 4 carbon atoms, or a combination thereof, and 2) a second high $T_g$ monomer comprising acrylamide, (meth)acrylonitrile, N-alkyl acrylamide having an alkyl group with 1 to 10 carbon atoms, N,N-dialkyl acrylamide having alkyl groups with 1 to 10 carbon atoms, or a combination thereof.

Embodiment 31 is the emulsion composition of any one of embodiments 1 to 30, further comprising C9-based hydrocarbon tackifier.

Embodiment 32 is the emulsion composition of embodiment 31, wherein the C9-based hydrocarbon tackifier is hydrogenated.

Embodiment 33 is the emulsion composition of any one of embodiments 1 to 32, wherein the droplets have an average diameter up to 2000 micrometers or up to 1000 micrometers or up to 500 micrometers.

Embodiment 34 is a latex composition comprising a polymerized product of the emulsion composition of any one of embodiments 1 to 33, wherein the latex composition comprises polymeric latex particles.

Embodiment 35 is the latex composition of embodiment 34 further comprising a tackifier.

Embodiment 36 is the latex composition of embodiment 35, wherein the tackifier is in the form of a dispersion.

Embodiment 37 is the latex composition of any one of embodiments 34 to 36, wherein the latex particle comprises both the second (meth)acrylate polymer and the polymerized product of the first monomer composition within the same latex particles.

Embodiment 38 is the latex composition of any one of embodiments 34 to 37, wherein the latex particle has a single glass transition temperature when measured using a Differential Scanning calorimeter.

Embodiment 39 is a pressure-sensitive adhesive comprising a dried product of the latex composition of any one of embodiments 34 to 38.

Embodiment 40 is an article comprising (a) a substrate and (b) a first pressure-sensitive adhesive layer positioned adjacent to a first major surface of the substrate, wherein the first pressure-sensitive adhesive layer comprises the pressure-sensitive adhesive of embodiment 39.

Embodiment 41 is the article of embodiment 40, further comprising a second layer of pressure-sensitive adhesive of embodiment 39 positioned adjacent to a second major surface of the substrate.

Embodiment 42 is the article of embodiment 40 or 41, wherein the substrate is a foam or polymeric film.

Embodiment 43 is the article of any one of embodiments 40 to 42, wherein the substrate is a biaxially oriented polyolefin film.

Embodiment 44 is the article of any one of embodiments 40 to 42, wherein the substrate is a release liner.

Embodiment 45 is the article of embodiment 44, wherein the release liner comprises a release coating comprising a polymerized product of a vinyl-silicone copolymer or a (meth)acrylate-functionalized siloxane.

Embodiment 46 is the article of embodiment 40 or 41, wherein the article is a transfer tape.

Embodiment 47 is the article of embodiment 40, wherein the article is an adhesive tape.

Embodiment 48 is the article of embodiment 47, wherein the adhesive tape is a packaging tape.

Embodiment 49 is a method of forming a pressure-sensitive adhesive. The method includes (a) forming an emulsion composition of any one of embodiments 1 to 33, (b) polymerizing the emulsion composition to form a latex composition comprising polymeric latex particles, and (c) drying the latex composition to form the pressure-sensitive adhesive.

Embodiment 50 is the method of embodiment 49 wherein forming the emulsion composition comprises forming a second (meth)acrylate polymer, dissolving the second (meth)acrylate polymer in one or more monomers in the first monomer composition to form a polymer solution, adding the polymer solution to the first phase, and forming droplets of the polymer solution within the first phase by mixing with high shear.

EXAMPLES

All parts, percentages, ratios, and the like used in the Examples are by weight unless indicated otherwise.

TABLE 1

Materials

| Designation | Description, Source |
|---|---|
| AA | Acrylic acid, which is an acidic monomer available from Dow Chemical (Midland, MI, USA) |
| BOPP | Biaxially-oriented polypropylene film, obtained from 3M Co. (St. Paul, MN, USA). Such films are further described in the following patents: U.S. Pat. No. 6,638,637, U.S. Pat. No. 6,451,425, U.S. Pat. No. 3,324,218, U.S. Pat. No. 3,241,662, and U.S. Pat. No. 5,032,460. A first major surface of the film was coated with a chlorinated polyolefin primer (18-23 weight percent chlorine) in toluene that was obtained from Eastman Chemical (Kingsport, TN, USA). The second major surface of the film was coated with a |

TABLE 1-continued

Materials

| Designation | Description, Source |
|---|---|
| | low adhesion backside, which was a solvent-based polyurethane that is commercially available from Mayzo (Suwanee, GA, USA). |
| CEA | Beta-carboxyethyl acrylate, which is an acidic monomer available from Cytec (Woodland Park, NJ, USA) |
| tDDM | Tert-dodecyl mercaptan, which is a chain transfer agent available from Arkema, Inc. (Calvert City, KY, USA) |
| EPOCROS WS-500 | Polyoxazoline (39 wt. % solution in water/1-methoxy-2-propanol), which is a crosslinker available from Nippon Shokubai Co., Ltd. (Osaka, Japan) |
| HITENOL BC-1025 | Polyoxyethylene alkylphenyl propenyl ether ammonium sulfate (25 wt. % solids solution in water), which is a polymerizable surfactant available from Dai-Ichi Kogyo Seiyaku Co., Ltd. (Japan) |
| IBOA | Isobornyl acrylate, which is a monomer available from San Esters Corp. (New York, NY, USA) |
| IOA | Isooctyl acrylate, which is a monomer available from 3M Co. (St. Paul, MN, USA) |
| IOTG | Isooctyl thioglycolate, which is a chain transfer agent available from Evans Chemetics (Teaneck, NJ, USA) |
| IRGACURE 651 | 2,2-Dimethoxy-1,2-diphenyl ethanone, which is an initiator available from BASF (Ludwigshafen, Germany) |
| IRGANOX 1010 | Pentaerythritol tetrakis (3-(3,5-di-tert-butyl-4-hydroxyphenyl) propionate), which is an antioxidant available from BASF (Ludwigshafen, Germany) |
| $K_2S_2O_8$ | Potassium persulfate, which is an initiator available from FMC BioPolymer (Rockland, ME, USA) |
| LUPERSOL 101 | 2,5-Dimethyl-2,5-di(t-butylperoxy)hexene, which is an initiator available from Atofina (Philadelphia, PA, USA) |
| LUPERSOL 130 | 2,5-Dimethyl-2,5-di(t-butylperoxy)hexyne-3, which is an initiator available from Atofina (Philadelphia, PA, USA) |
| MAA | Methacrylic acid, which is a monomer available from Dow Chemical (Midland, MI, USA) |
| MEHQ | Methoxyether hydroquinone, which is an inhibitor available from Solvay (Rhodia) (University Park, IL, USA) |
| $Na_2HPO_4$ | Sodium phosphate, which is a dibasic salt available from Innophos (Cranbury, NJ, USA) |
| $NH_4OH$ | Ammonium hydroxide (30 wt. % solution), which is a base available from J. T. Baker (USA) |
| 2-OA | 2-octyl acrylate, which is a monomer available from 3M Co. (St. Paul, MN, USA) |
| OACM | Octyl acrylamide (N-tert-octyl acrylamide), which is a monomer available from National Starch (Bridgewater, NJ, USA) |
| PARAGUM 500 | Alkali swellable polyacrylate thickener from Para-Chem, a Royal Adhesives and Sealants Company (South Bend, IN, USA) |
| PICCOTAC 6095E | Modified aliphatic hydrocarbon resin, stabilized with 2,6-di-tert-butyl-para-cresol antioxidant, available from Eastman Chemical Co. (Kingsport, TN, USA) |
| SNOWTACK SE780G | Tackifier resin that is commercially available from Lawter (Chicago, IL, USA) |
| VAZO 52 | 2,2'-Azobis (2,4-dimethylpentanenitrile), available from DuPont (Wilmington, DE, USA) |
| VAZO 67 | 2,2'-Azobis (2-methylbutanenitrile), available from DuPont (Wilmington, DE, USA) |
| VAZO 88 | 1,1'-Azobis (cyclohexanecarbonitrile), available from DuPont (Wilmington, DE, USA) |
| PICCOTAC 6095E | A hydrocarbon tackifying resin having a Mw of 1700 Daltons that is available from Eastman (Kingsport, TN, USA) |

Test Method 1: Polymer Molecular Weight Measurement

The weight average molecular weight (Mw) of the prepared polymers was measured via size exclusion chromatography (SEC). A polymer sample of 50 milligrams of solids was dissolved in 10 mL of tetrahydrofuran (THF that was inhibited with 250 ppm butylated hydroxytoluene (BHT)). The resulting solution was filtered through a 0.45 micrometer syringe filter and then analyzed by SEC. The SEC system was operated under the following conditions:

Sample Injection: 10 microliters
Mobile Phase: THF, EMD OMNISOLV GRADE or equivalent (no inhibitor)
Flow Rate: 1.0 mL/minute
System: Waters e2695 pump/autosampler
Detector: Waters 2414 evaporative light scattering detector (70° C. drift tube, 30 psi (approximately 207 kPa) nitrogen flow, 30° C. nebulizer temperature
Columns: Four PL-GEL columns, each 300 mm by 7.8 mm having pore sizes of $10^4$, $10^3$, 500, and 100 Angstroms that are available from Agilent Technologies (Santa Clara, Calif., USA). The columns were held at 40° C. using a column heater.
Standards: Polystyrene standards having a narrow molecular weight distribution and having an average molecular weight peak ranging from 377,400 to 580 Daltons were used to establish a calibration curve (3rd order polynomial fit).
Syringe filter: 0.45 micrometer polytetrafluoroethylene The samples were run and effective molecular weight distribution plots were calculated using the narrow molecular weight polystyrene standards for calibration. A lower molecular weight cut-off of 500 Daltons was used in processing the data. Number average molecular weight (Mn), weight average molecular weight (Mw), and polydispersity index (Mw/Mn) values were obtained for each sample run.

Test Method 2: Polymer Viscosity Measurement

Polymer viscosity was measured with a Brookfield viscometer (obtained from Brookfield Engineering, Middleboro, Mass., USA), using spindle 2 at a rotating speed of 30 revolutions per minute.

Test Method 3: Weight Percent Solids Measurement

To measure solids content of various samples, about 1 gram of the sample (e.g., wet latex or polymer solution) was put into an aluminum dish and weighed. Then the dish and sample were dried at 105° C. (unless otherwise indicated) for 2 hours.

When the sample was analyzed to determine the weight percent (wt. %) of latex particles (weight percent solids of the latex composition), the following equation was used:

Latex solid wt. %=100×(Weight of dry latex polymer)/(Weight of wet latex polymer)

The weight of wet latex polymer refers to the weight of the latex prior to drying. The weight of dry latex refers to the weight of the latex polymer after drying.

When the sample was analyzed to determine the amount of the second (meth)acrylate in a monomer solvent (e.g., 2-OA, also used as part of the first monomer composition), the following equation is used:

Polymer solution solid wt. %=100×(Weight of dry polymer)/(Weight of polymer solution)

The weight of the polymer solution refers to the weight before drying and includes the total the weight of the monomer solvent and the second (meth)acrylate polymer. The weight of dry polymer refers to the weight after drying and typically includes only the second (meth)acrylate polymer.

Test Method 4: Latex pH Measurement

The latex pH was measured with a pH meter (from Chemtrix, Rolling Hills Estates, CA, USA under the trade designation MODEL 60A pH METER).

Test Method 5: Glass Transition of Polymer ($T_g$) by Differential Scanning Calorimetry (DSC)

Polymer samples were dried to remove water and any organic solvent that was present. The dried samples were then weighed and loaded into TA Instruments $T_{zero}$ aluminum hermetic DSC sample pans. The samples were analyzed using a TA Instruments Q2000 MODULATED DIFFERENTIAL SCANNING CALORIMETER ("Q2000 MDSC", including a RC-03761 sample cell), utilizing a heat-cool-heat method in temperature-modulated mode (−90° C. to 125° C. at 5° C./min. with a modulation amplitude of ±0.796° C. and a period of 60 seconds) under a nitrogen atmosphere.

In temperature modulated mode, the Q2000 MDSC gave three signals: cumulative (standard) heat flow, reversing (Rev) heat flow, and nonreversing (Nonrev) heat flow. The cumulative heat flow signal was the sum of the reversing and nonreversing heat flow signals. The reversing signal was the heat capacity ($C_p$) component and included transitions such as the $T_g$ (glass transition). The nonreversing signal was the kinetic component and included kinetic transitions such as crystallization and chemical reactions.

Following data collection, the thermal transitions were analyzed using the TA UNIVERSAL ANALYSIS program. If present, any glass transitions ($T_g$) or significant endothermic or exothermic peaks were evaluated. The glass transition temperatures were evaluated using the step change in the standard heat flow (HF) or reversing heat flow (Cp related/Rev HF) curves. The onset, midpoint (half height), and end temperatures of the transition were noted as well as the change in heat capacity observed at the glass transition were calculated. Any peak transitions were evaluated using the heat flow (HF), reversing heat flow (Rev HF) or non-reversing heat flow (Nonrev HF) curves. Peak area values and/or peak minimum/maximum temperatures were also determined. The peak integration results were normalized for sample weight and reported in Joules per gram (J/g).

Test Method 6: Particle Size

An average particle size of latex samples was measured with dynamic light scattering instrument (ZETASIZER NANO ZS, available from Malvern Instruments Ltd. (Worcestershire, UK)) with diluted latex sample (approximately one drop of latex in 5 mL of water), following the manufacturer's instructions, and using polystyrene bead calibration standards.

Test Method 7: Peel Adhesion Test—PSA-Coated Polyester Tape

A sample of pressure-sensitive adhesive to be tested was coated with a hand-spread knife onto a 2.0 mil (approximately 51 micrometer) polyester film (HOSTAPHAN 3 SAB, primed PET film, available from Mitsubishi Polyester Film Inc. (Greer, S.C., USA)), and dried in a 65° C. oven for 30 minutes to give a dry PSA thickness in a range of 0.9 to 1.2 mil (approximately 23 to 30 micrometers). The coated film was conditioned at 23° C. and 50 percent relative humidity for 24 hours, and then cut into strips of tape that were 1 inch (approximately 2.5 cm) wide.

The 1 inch (approximately 2.5 cm) wide strips of tape were applied to a stainless steel plate and then peel adhesion was assessed with a SLIP/PEEL TESTER MODEL 3M90 (obtained from Instrumentors Supply, Inc. (Oregon City, Oreg., USA)), using a peel angle of 180° and speed of 12 inches (approximately 30 cm) per minute. Peel adhesion values were reported as the average of three runs and were reported as both ounces per inch (oz/in) and Newtons per decimeter (N/dm).

Test Method 8: Fiberboard Shear Test—PSA-Coated Polyester Tape

A sample of pressure-sensitive adhesive to be tested was coated with a hand-spread knife onto a 2.0 mil (approximately 51 micrometer) polyester film (HOSTAPHAN 3 SAB, primed PET film, available from Mitsubishi Polyester Film Inc. (Greer, S.C.)), and dried in a 65° C. oven for 30 minutes to give a dry PSA thickness in a range of 0.9 to 1.2 mil (approximately 23 to 30 micrometers). The coated film was conditioned at 23° C. and 50 percent relative humidity for 24 hours, and then cut into strips of tape 0.5 inch (approximately 1.3 cm) wide.

Fiberboard was adhered to a stainless steel plate using a double sided tape. Then the 0.5 inch (approximately 1.3 cm) wide strip of the test PSA tape was adhered by the PSA side to the surface of the fiberboard, being pressed on with a 2 kilogram roller, providing a contact area of 0.5 inch by 0.5 inch (approximately 1.3 cm by 1.3 cm). A hanging weight of 1 kilogram was attached to the test PSA tape, and time to a shear failure of the test PSA tape was noted.

Test Method 9: Fiberboard Shear Test with Aged Samples

A sample of pressure-sensitive tape to be tested was prepared as in the Fiberboard Shear Test, except that the sample was conditioned at 23° C. and 50 percent relative humidity for 2 to 3 weeks.

Fiberboard was adhered to a stainless steel plate using a double sided tape. Then the 0.5 inch (approximately 1.3 cm) wide strip of the test PSA tape was adhered by the PSA side to the surface of the fiberboard, being pressed on with a 2 kilogram roller, providing a contact area of 0.5 inch by 0.5 inch (approximately 1.3 cm by 1.3 cm). A hanging weight of 1 kilogram was attached to the test PSA tape, and time to a shear failure of the test PSA tape was noted.

Preparatory Example 1 (PE-1)

In a first step of the polymerization, a 5 liter stainless steel reactor was charged with a 2 kilogram mixture consisting of 300 grams of IOA, 1600 grams of IBOA, and 100 grams of AA, along with 2 grams of IRGANOX 1010, 50 grams of chain transfer agent IOTG, 0.4 grams of MEHQ, and 0.12 grams of VAZO 52. The reactor was sealed, purged of oxygen with nitrogen, and then held at approximately 5 psig nitrogen pressure. The reaction mixture was heated in a first step to 60° C. and the reaction proceeded adiabatically. The temperature peaked at 149° C. When the reaction was complete, the mixture was cooled to below 50° C.

A solution of various initiators (0.36 grams of VAZO 52, 0.08 grams of VAZO 67, 0.12 grams of VAZO 88, 0.12 grams of LUPERSOL 101, and 0.16 grams of LUPERSOL 130) dissolved in a minimal amount ethyl acetate and 25 grams of IOTG was then added to the reaction product of the first step. The reactor was sealed and purged of oxygen with nitrogen, and then held at 5 psig nitrogen pressure. The reaction mixture was heated to 60° C. and the reaction proceeded adiabatically. After the reaction reached peak temperature of 120° C., the mixture was heated to 180° C. for 2 hours and drained, while hot, into aluminum trays. After the material cooled, the resulting solid polymer was hammered into flakes. The weight average molecular weight of the resulting (meth)acrylate polymer (PE-1) was determined according to the polymer molecular weight measurement of Test Method 1 to be about 7260 grams/mole.

A 40 gram sample of PE-1 and 160 grams of 2-octyl acrylate were added into 8-oz (approximately 237 mL) glass jar. The jar was capped and placed on a roller for the polymer to dissolve. This resulted in a polymer solution having about 20 weight percent solids and 8 cps Brookfield viscosity.

Comparative Preparatory Example 1 (CPE-1)

An 8-oz (approximately 237 mL) glass bottle was charged with 38 grams of IOA, 2 grams of AA, 0.6 grams of IOTG, and 0.02 grams of VAZO52. After being purged with nitrogen for 3 minutes, the bottle was capped and placed in a Launderometer set at 75° C. for 16 hours, and then set at 85° C. for 2 hours.

After being cooled to room temperature, the bottle was opened and 160 grams of 2-OA was added. The bottle was placed on a roller for the polymer to dissolve. This resulted in a polymer solution of 18.8 weight percent solids determined according to Test Method 3. The weight average molecular weight of the (meth)acrylate polymer was determined according to Test Method 1 to be about 37,960 grams/mole.

Preparatory Examples 2, 3, and 4 (PE-2, PE-3, PE-4) and Comparative Preparatory Example 2 (CPE-2)

Polymers PE-2, PE-3, PE-4 and CPE-2 were made using the same procedure as in CPE-1, except using the compositions listed in Table 2, which includes the resulting weight average molecular weights and Brookfield viscosity values.

Preparatory Example 5 (PE-5)

An 8-oz (approximately 237 mL) glass bottle was charged with 45 grams of IOA, 50 grams of IBOA, 5 grams of AA, 0.8 grams of t-DDM, and 0.1 grams of IRGACURE 651. Content in the jar was stirred under nitrogen purge and irradiated with a GE F15T8-BLB 15W Black-Ray lamp for 20 minutes, forming a viscous syrup. The syrup was about 72 percent polymerized. A 40 grams portion of syrup from this reaction was then poured into a separate 8-oz (approximately 237 mL) jar, and 123 grams of 2-OA was added. The jar was placed on a roller for the syrup to dissolve, resulting in a polymer solution of 17.7 percent solids as determined according to Test Method 3. The weight-average molecular weight of polymer was determined according to Test Method 1 to be about 67,010 grams/mole.

TABLE 2

Preparatory Examples of the Second (Meth)acrylate Polymers

| Sample | Composition (weight ratio) | Initiator | Mw (g/mole) | Brookfield Viscosity of Sample dissolved in 2-OA, cps (weight percent solids) | Calculated $T_g$ (° C.) from Fox Equation |
|---|---|---|---|---|---|
| PE-1 | IOA-IBOA-AA-IOTG (15:80:5:2.5) | multiple | 7,260 | 8 cps (at 20 wt. %) | 60 |
| PE-2 | IOA-IBOA-AA-IOTG (70:20:5:1.5) | VAZO 52 | 31,040 | 13 cps (at 17.7 wt. %) | −16 |
| PE-3 | IOA-IBOA-IOTG (80:20:1.5) | VAZO 52 | 29,020 | 11 cps (at 17.1 wt. %) | −36 |
| PE-4 | IOA-OACM-IOTG (80:20:1.5) | VAZO 52 | 48,630 | 14 cps (at 16.9 wt. %) | −35 |
| PE-5 | IOA-IBOA-AA-tDDM (45:50:5:0.8) | IRGACURE 651 | 67,010 | 24 cps (at 17.7 wt. %) | 8 |
| CPE-1 | IOA-AA-IOTG (95:5:1.5) | VAZO 52 | 37,960 | 15 cps (at 18.8 wt. %) | −50 |
| CPE-2 | IOA-tDDM (100:0.8) | VAZO 52 | 78,100 | 20 cps (at 17.5 wt. %) | −55 |

Example 1 (EX-1)

A 15.6 gram portion of HITENOL BC-1025, 1.63 grams of sodium phosphate dibasic salt, and 280 grams of deionized water were added into a 1.5-liter plastic beaker and stirred to form an aqueous solution. 270 grams of 2-OA, 6.5 grams of AA, 16.3 grams of CEA, and 32.5 grams of the polymer solution containing PE-1 (see Table 2, used as 20 weight percent solids in 2-OA) were added to a 600-mL plastic beaker and stirred to form a monomer solution (e.g., the monomer solution contained the monomers of the first monomer solution and the dissolved second (meth)acrylate polymer). The monomer solution was poured into the aqueous solution and mixed well. The resulting mixture was poured into a 1-liter stainless steel WARING blender container. The mixture was then homogenized with the blender at high speed setting for 2 minutes then poured into a 2-liter resin flask equipped with a thermometer, mechanical agitator with glass retreat blade impeller, condenser, and nitrogen inlet tube. A 0.3 gram portion of $K_2S_2O_8$ was then added. The reaction mixture was stirred at 300 rpm under a blanket of nitrogen, heated to 60° C., and then held at 60° C. for 6 hours. The reaction product was then cooled and filtered through cheesecloth to give latex composition EX-1 having 52.0 weight percent solids, a Brookfield viscosity of 365 cps, a pH of 3.8, and a particle diameter of 530 nm. The latex composition was evaluated as a PSA and the results were as summarized in Table 3.

Examples 2 to 4 (EX-2 to EX-4)

Latex compositions were made the same way as in Example 1, except using different first monomer compositions as listed in Table 3. The latex composition was evaluated as a PSA and the results were as summarized in Table 3. The particle diameter for EX-2 material was 340 nm, and the particle diameter for the EX-3 material was 530 nm.

Example 4A (EX-4A)

A 40 gram portion of the latex composition from Example 4 was added into a 4-oz (approximately 120 mL) plastic jar. To the sample, 0.2 grams of $NH_4OH$ was added, and the mixture was stirred well. A 0.064 gram sample of a solution consisting of 0.016 grams of EPOCROS WS-500 and 0.048 grams of deionized water was then added, and the mixture was stirred well to give the latex composition EX-4A having a pH 4.8. The latex composition was evaluated as a PSA and the results were as summarized in Table 3.

Examples 5 to 8 (EX-5 to EX-8)

Latex composition samples were made the same way as in Example 1, except that different polymer solutions were used in place of "PE-1" polymer solution, with adjustment for solids content. Compositions and results of PSA testing were as summarized in Table 3.

Comparative Example 1 (CE-1)

Latex composition preparation CE-1 was attempted following the method described in Example 1, except that carboxyethyl acrylate was removed from the formulation and replaced by same amount of acrylic acid. Results were as summarized in Table 3.

Comparative Examples 2 to 4 (CE-2 to CE-4)

Latex adhesives CE-2 to CE-4 were made the same way as in Example 1, except that different polymer solutions were used in place of the PE-1 polymer solution in Example 1 and adjusted for solids content. Compositions and results were as summarized in Table 3.

Comparative Example 5 (CE-5)

Latex composition preparation was attempted in the same was as Example 1, except that 3.9 grams of sodium dodecylbenzene sulfonate, which is a surfactant without a polymerizable group, was used in place of the HITENOL BC1025. Attempted polymerization resulted in formation of coagulum.

Comparative Example 6 (CE-6)

Latex composition preparation was attempted in the same was as Example 1, except that 2-octyl acrylate was substituted (in the same amount) in place of PE-1. That is, this comparative example did not include the second (meth) acrylate polymer. Attempted polymerization resulted in formation of coagulum.

TABLE 3

Adhesive Properties of EX-1 to EX-8 and CE-1 to CE-4

| Sample | Composition (weight ratio) | pH | Peel Adhesion, oz./inch (N/dm) | Fiberboard Shear, minutes | Fiberboard Shear with Aged Samples, minutes |
|---|---|---|---|---|---|
| EX-1 | 2-OA:AA:CEA:(PE-1) (91:2:5:2) | 3.8 | 31 (34) | 178 | 5619 |
| EX-2 | 2-OA:MAA:CEA:(PE-1) (91:2:5:2) | 4.3 | 35 (38) | 242 | 7804 |
| EX-3 | 2-OA:AA:CEA:(PE-1) (89:2:5:4) | 3.8 | 33 (36) | 234 | 3917 |
| EX-4 | 2-OA:AA:MAA:CEA:(PE-1) (90:2:1:5:2) | 3.9 | 37 (40) | 200 | 1155 |
| EX-4A | EX-4 + $NH_4OH$ + EPOCROS WS-500 (see description) | 4.8 | 33 (36) | >20000 | NA |
| EX-5 | 2-OA:AA:CEA:(PE-5) (91:2:5:2) | 4.0 | 30 (33) | 40 | 1373 |
| EX-6 | 2-OA:AA:CEA:(PE-2) (91:2:5:2) | 3.9 | 29 (32) | 62 | 2513 |
| EX-7 | 2-OA:AA:CEA:(PE-3) (91:2:5:2) | 3.9 | 26 (28) | 105 | 1928 |
| EX-8 | 2-OA:AA:CEA:(PE-4) (91:2:5:2) | 3.7 | 27 (30) | 90 | >20000 |

TABLE 3-continued

Adhesive Properties of EX-1 to EX-8 and CE-1 to CE-4

| Sample | Composition (weight ratio) | pH | Peel Adhesion, oz./inch (N/dm) | Fiberboard Shear, minutes | Fiberboard Shear with Aged Samples, minutes |
|---|---|---|---|---|---|
| CE-1 | 2-OA:AA:(PE-1) (94:4:2) | 3.6 | 22 (24) | 738 | 619 |
| CE-2 | 2-OA:AA:CEA:(PICCOTAC 6095E) (91:2:5:2) | 3.8 | 20 (22) | 5 | 6 |
| CE-3 | 2-OA:AA:CEA:(CPE-2) (91:2:5:2) | 3.9 | 22 (24) | 87 | 697 |
| CE-4 | 2-OA:AA:CEA:(CPE-1) (91:2:5:2) | 3.9 | 25 (27) | 74 | 356 |

In Table 3, "NA" means not analyzed. The Peel Adhesion was measured according to Test Method 7. The Fiberboard Shear was measured according to Test Method 8, and the Fiberboard Shear with Aged Samples was measured according to Test Method 9.

Additional examples of polymeric emulsions (EX-9 to EX-12) were provided using modified conditions, in particular using a larger batch size compared to Example 1 and different reactor conditions.

Example 9 (EX-9)

A 15.6 gram portion of HITENOL BC1025, 1.63 grams of sodium phosphate dibasic salt, and 280 grams of deionized water were added into a 1.5-liter plastic beaker and stirred to form an aqueous solution. 270 grams of 2-octyl acrylate (2-OA), 6.5 grams of acrylic acid (AA), 16.3 grams of 2-carboxylethyl acrylate (CEA), and 32.5 grams of the polymer solution containing PE-1 (see Table 2, used as 20 weight percent solids in 2-OA) were added to a 600-mL plastic beaker and stirred to form a monomer solution. The monomer solution was poured into the aqueous solution and mixed well. The resulting mixture was poured into a 1-liter stainless steel WARING blender container. The content was homogenized with the blender at high speed setting for 2 minutes to form a stable emulsion. The mixing and homogenization was repeated to provide a second batch of homogenized emulsion, and the two batches of homogenized emulsion were then poured into a 2-liter resin flask equipped with a thermometer, mechanical agitator with glass retreat blade impeller, condenser and nitrogen inlet tube. A 0.6 gram portion of $K_2S_2O_8$ was then added. The reaction mixture was stirred at 300 rpm under nitrogen blanket and heated to 60° C. After 25 minutes at 60° C., a reaction exotherm brought the batch to peak temperature of 80° C. The batch was then heated to 85° C. and maintained at that temperature for 2 hours, cooled and filtered through cheesecloth to give a latex composition having 52.5 weight percent solids, Brookfield viscosity of 310 cps, a pH of 3.9, and an average particle size of 460 nm.

The $T_g$ of the EX-9 polymer was measured according to Test Method 5. The $T_g$ value was −40.2° C., which was obtained from the corresponding DSC shown in FIG. 1. More particularly, FIG. 1 shows the modulated DSC reversible heat flow signals from the second heating (2H) cycle is plotted as a function of temperature in a nitrogen atmosphere.

Example 9A (EX-9A)

Into an 800-mL plastic beaker was added 480 grams of the latex composition from Example 9. Then, 4 grams of $NH_4OH$ was added under mechanical agitation. This resulted in a latex composition having a Brookfield viscosity of 620 cps and pH 4.7. The latex composition was evaluated as a PSA and the results are summarized in Table 4.

Example 9B (EX-9B)

240 grams of the latex composition from Example 9A was added into 8-oz (approximately 237 mL) plastic jar. Then, 0.36 grams of a solution consisting of 0.09 grams of EPO-CROS WS-500 and 0.27 grams of deionized water was then added and stirred well. The resulting latex composition had a Brookfield viscosity of 640 cps and pH 4.7. The latex composition was evaluated as a PSA and the results were as summarized in Table 4.

Example 10 (EX-10)

A latex composition was made the same way as in Example 9, except for different monomer compositions. The latex composition was evaluated as a PSA and the results were as summarized in Table 4.

Figure 2:
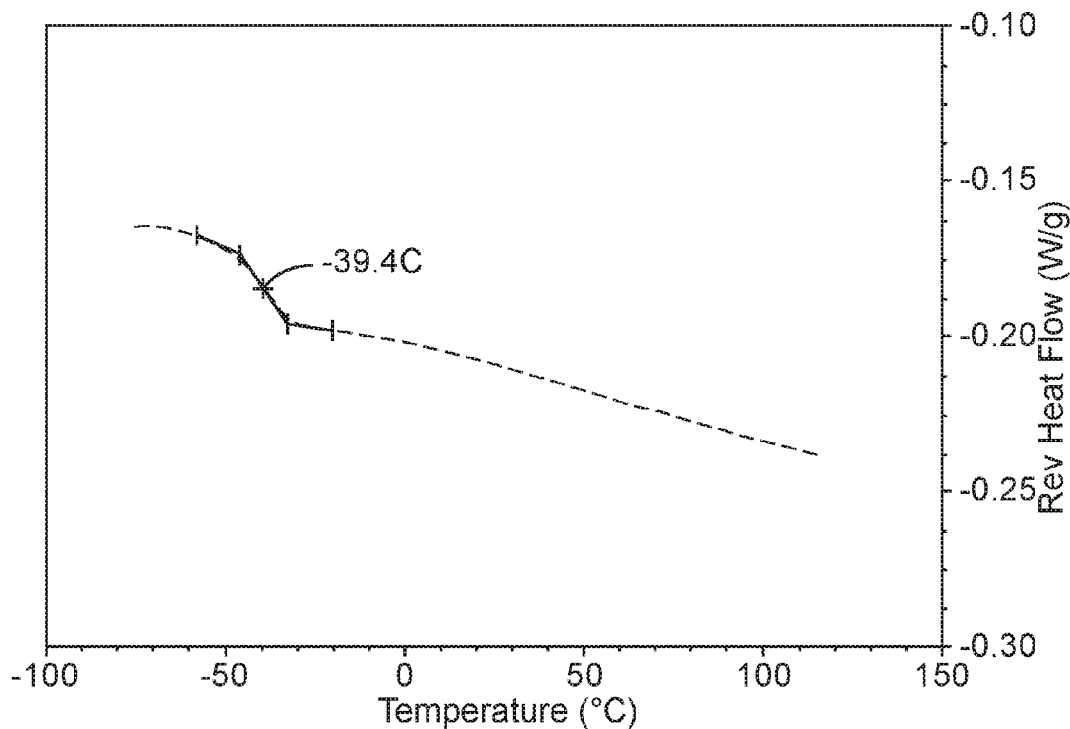
FIG. 2 is a plot of reversible heat flow (obtained during the second heating cycle using Modulated Differential Scanning calorimetry) versus temperature for the dry polymeric material of Example 10.

The $T_g$ and DSC of the EX-10 polymer were measured according to Test Method 5. The $T_g$ value was −39.4° C., and the corresponding DSC was as shown in FIG. 2. More particularly, FIG. 2 shows the modulated DSC reversible heat flow signals from the second heating (2H) cycle is plotted as a function of temperature in a nitrogen atmosphere.

Example 10A (EX-10A)

Into an 800-ml plastic beaker was added 480 grams of the latex composition from Example 10. Then, 2.4 grams of $NH_4OH$ was added under mechanical agitation. This resulted in a latex composition having a Brookfield viscosity of 660 cps and pH 4.8. The latex composition was evaluated as a PSA and the results were as summarized in Table 4.

Example 11 (EX-11)

A 60 gram portion of the latex composition from Example 9 was added into a 2-oz (approximately 58 mL) plastic jar. Then, 0.94 grams of $NH_4OH$ was added into the sample and stirred well. This resulted in a latex composition having a Brookfield viscosity of 1140 cps and pH 6.7. The latex composition was evaluated as a PSA and the results were as summarized in Table 4.

Example 12 (EX-12)

A 60 gram portion of the latex composition from Example 10 was added into a 2-oz plastic jar. Then, 0.94 grams of NH$_4$OH was added into the sample and stirred well. This resulted in a latex composition having a Brookfield viscosity of 1120 cps and pH 6.5. The latex composition was evaluated as a PSA and the results were as summarized in Table 4.

to the measurements, all rolls of tapes were equilibrated overnight in a constant temperature and humidity room (23° C. and 50 percent relative humidity). The peel adhesion and shear resulting test data for adhesives resulting from EX-9, EX-9A, and EX-9B was as summarized in Table 5.

TABLE 4

Adhesive Properties of EX-9 to EX-12

| Sample | Composition (weight ratios) | pH | Peel Adhesion, oz./inch (N/dm) | Fiberboard Shear, minutes | Fiberboard Shear with Aged Samples, minutes |
|---|---|---|---|---|---|
| EX-9 | 2-OA:AA:CEA:(PE-1) (91:2:5:2) | 3.9 | NA | NA | NA |
| EX-9A | Example 9 + NH$_4$OH (see description) | 4.7 | 33 (36) | 65 | 525 |
| EX-9B | Example 9A + EPOCROS WS-500 (see description) | 4.7 | 32 (35) | 74 | 889 |
| EX-10 | 2-OA:AA:MAA:CEA: (PE-1) (90:2:1:5:2) | 3.9 | 39 (43) | 137 | 260 |
| EX-10A | Example 10 + NH$_4$OH (see description) | 4.8 | 37 (40) | 147 | 904 |
| EX-11 | Example 9 + NH$_4$OH (see description) | 6.7 | 30 (33) | 85 | 413 |
| EX-12 | Example 10 + NH$_4$OH (see description) | 6.5 | 35 (38) | 120 | 774 |

In Table 4, "NA" means not analyzed. The Peel Adhesion was measured according to Test Method 7. The Fiberboard Shear was measured according to Test Method 8, and the Fiberboard Shear with Aged Samples was measured according to Test Method 9.

Making and Testing Rolls of "Packaging Tape" from EX-9, EX-9A, and EX-9B

Pressure-sensitive adhesives prepared from each of Examples 9, 9A and 9B were used to make "packaging tape" rolls according to the following procedure. A sample of the latex composition was coated on the primed side of a 1.95-mil (approximately 50 micrometers) thickness biaxially oriented polypropylene BOPP film having a low adhesion backside and a primed side. Coating speed for application of the latex composition was about 10 feet per minute (approximately 3 meters per minute), and the coated film was dried at 65° C. in a forced air oven for about 5 minutes. The dry thickness of the adhesive was about 0.66 mils (approximately 17 micrometers). Upon slitting and converting, 2-inch (approximately 5.1 cm) wide rolls of "packaging tape" were obtained, and subjected to the following test procedures for peel adhesion and shear.

Tape properties including peel adhesion on stainless steel (according to Test Method 7) and shear on fiberboard for "initial" and "aged" rolls were measured according Test Methods 8 and 9, respectively, except that for the "aged" rolls, two aging conditions were used, as indicated in Table 5: 120° F. (approximately 49° C.) for 4 weeks, and 90° F. (approximately 32° C.) and 90% humidity for 4 weeks. Prior

TABLE 5

Peel Adhesion and Shear Test Data for "Packaging Tapes"

| Sample | Peel Adhesion, oz./inch (N/dm) | Aged Peel Adhesion—Test A, oz./inch (N/dm) | Aged Peel Adhesion—Test B, oz./inch (N/dm) | Fiberboard Shear, minutes | Fiberboard Shear with Aged Samples—Test A, minutes | Fiberboard Shear with Aged Samples—Test B, minutes |
|---|---|---|---|---|---|---|
| EX-9 | 27 | 28 (31) | 32 (35) | 418 | 17023 | 3127 |
| EX-9A | 27 | 28 (31) | 29 (32) | 616 | 13130 | 6697 |
| EX-9B | 27 | 28 (31) | 28 (31) | 17871 | 12842 | 17038 |

In Table 5, the Peel Adhesion was measured according to Test Method 7. The Aged Peel Adhesion—Test A was measured according to Test Method 7 except that the samples were conditioned at 49° C. for 4 weeks while the Aged Peel Adhesion—Test B was measured according to Test Method 7 except that the samples were conditioned at 32° C. and 90 percent relative humidity for 4 weeks. The Fiberboard Shear was measured according to Test Method 8, the Fiberboard Shear with Aged Samples—Test A was measured according to Test Method 9 except that the samples were conditioned at 49° C. for 4 weeks, and the Fiberboard Shear with Aged Samples—Test B was according to Test Method 9 except that the samples were conditioned at 32° C. and 90 percent relative humidity for 4 weeks.

Making and Testing "Transfer Tape" from EX-11 and EX-12

Pressure-sensitive adhesives prepared from the latex composition of EX-11 and EX-12 were used to make "transfer tapes" according to the following procedure. A sample of the latex composition was coated with a hand-spread knife coater on a silicon release liner (available from Itasa Co., Andoain, Spain, under the trade designation "M30"), and dried in a 65° C. oven for 30 minutes to give dry PSA thickness of 1.9 to 2.2 mil (approximately 48 to 56 micrometers). Another silicone release liner was placed on top of the dried PSA coating. After conditioning in a constant temperature and humidity (23° C. and 50% relative humidity) room for 1 week, the release liner was peeled off and the PSA layer was transferred to a 1 mil (approximately 25 micrometer) polyester film to form a laminated adhesive sheet. The laminated adhesive sheets were cut into strips and tested for peel adhesion on a stainless steel plate, according to Test Method 7.

Shear testing of the "transfer tapes" prepared from EX-11 and EX-12 was performed on a stainless steel plate with a 0.5 inch by 0.5 inch (approximately 1.3 cm by 1.3 cm) contact area and with a 500 gram load at 70° C. The peel adhesion and shear resulting test data for pressure-sensitive adhesives formed from EX-11 and EX-12 were as summarized in Table 6.

TABLE 6

Peel Adhesion and Shear Test Data for "Transfer Tapes"

| Sample | Composition (weight ratios) | pH | Peel Adhesion on stainless steel, oz./inch (N/dm) | Shear on stainless steel, minutes |
|---|---|---|---|---|
| EX-9 | 2-OA:AA:CEA:(PE-1) (91:2:5:2) | 3.9 | NA | NA |
| EX-10 | 2-OA:AA:MAA:CEA: (PE-1) (90:2:1:5:2) | 3.9 | NA | NA |
| EX-11 | Example 9 + NH$_4$OH (see description) | 6.7 | 33 (36) | >7000 |
| EX-12 | Example 10 + NH$_4$OH (see description) | 6.5 | 31 (34) | >7000 |

Example 13 (EX-13)

A 30 gram sample of the latex composition of EX-9 was blended with 0.18 grams of PARAGUM 500 thickener. The resulting latex composition blend was used in making a "transfer tape" as described in Example 15.

Example 14 (EX-14)

A 30 gram sample of the latex composition of EX-9 was blended with 0.106 g of PARAGUM 500 thickener and 6 grams of SNOWTACK SE780G (i.e., the ratio of EX-9 polymer to tackifier was about 100:20). The resulting latex composition blend was used in making a "transfer tape" as described in Example 16.

Preparatory Example 6 (PE-6): Preparation of a Short-Wave UV-Cured Liner

A blend consisting of 70 wt. % RC-902, a silicone acrylate with a high silicone to acrylate ratio, and 30 wt. % RC-711, a silicone acrylate with a low silicone to acrylate ratio, both available from Evonik North America, Inc. (Parsippany, N.J., USA) was coated onto one side of a 50 micrometer thick unprimed PET film substrate (available from Mitsubishi Polyester Film, Inc., Greer, S.C.) to give a wet coating thickness of less than 1.0 micrometer. The coated film was then exposed to the output of three 150 W low-pressure mercury amalgam lamps, with a peak intensity at 185 nm, manufactured by Heraeus Noblelight (Hanau, Germany) in a nitrogen atmosphere at a speed of 15.2 meters per minute (mpm) to provide a short-wave UV-cured liner having a cured release surface. Other information about this liner can be found in U.S. Patent Application Publication No. 2013/0059105 (Wright et al.).

Example 15 (EX-15)

A sample of the latex composition blend of EX-13 was coated with a hand-spread knife coater onto the cured release surface of a sample of the short-wave UV-cured liner of PE-6, and then dried in 70° C. oven for 20 minutes to give a "transfer tape" having a latex PSA layer with dry thickness of about 2 mil (about 51 micrometers).

Example 16 (EX-16)

A sample of the latex composition blend of EX-14 was coated with hand-spread knife coater onto the cured release surface of a sample of the short-wave UV-cured liner of PE-6, and then dried in 70° C. oven for 20 minutes to give a "transfer tape" having a latex PSA layer with dry thickness of about 2 mil (about 51 micrometers).

Preparation of Test Samples from EX-15 and EX-16 "Transfer Tapes" for Release and Re-Adhesion Testing Samples of "transfer tape" from Examples 15 and 16 were aged and/or conditioned under one of the three following conditions:

Condition 1: 23° C. at 50% relative humidity for 24 hours.

Condition 2: 23° C. at 50% relative humidity for 24 hours, followed by 32° C. at 90% RH for 48 hours, and then equilibrating for 1 hour at 23° C. at 50% relative humidity.

Condition 3: 23° C. at 50% relative humidity for 24 hours, followed by heating in a 70° C. oven (humidity not controlled) for 48 hours, and then equilibrating for 1 hour at 23° C. at 50% relative humidity.

After the conditioning step, a 25 micrometer (1 mil) primed PET film was laminated to the conditioned latex PSA layer to form laminated test samples. The primed PET film was prepared by application of a sol-gel primer as described in Japanese Patent 02200476-A and as further described in U.S. Pat. No. 5,204,219 (Van Ooij et al.), European Patent No. 0301827 B1 (Woo et al.), and European Patent No. 0372756 (Strobel et al).

Test Method 10: Release Testing of the PET-backed "transfer tapes" of Examples 15 and 16

The peel adhesion value was a measure of the force required to pull the PET-backed adhesive tape from the short-wave UV-cured liner at an angle of 180° at a rate of 30.5 cm/min (12 inches/minute). The IMASS MODEL SP2000 PEEL TESTER (IMASS Corp., Accord, Mass.) was used to record the peel adhesion value, summarized as "Release" value in Table 7.

Test Method 11: Re-Adhesion Testing of the "Transfer Tapes" of Examples 15 and 16

To determine the re-adhesion value, PET-backed tape samples were peeled from the short-wave UV-cured liner using the Release Testing Method (Test Method 10), and the resulting PET-backed tape was then applied to the surface of a clean stainless steel panel. The PET-backed tape sample was rolled down against the panel by means of two passes with a 2 kg rubber roller at 61 cm/min (24 inches/min). The re-adhesion value was a measure of the force required to pull the PET-backed tape from the steel surface at an angle of 180° at a rate of 30.5 cm/min (12 inches/minute). The IMASS MODEL SP2000 PEEL TESTER was used to record the peel force, summarized as "Re-adhesion" value in Table 7.

TABLE 7

Release and Re-adhesion Testing of EX-15 and EX-16

| "Transfer Tape" Sample | Condition 1 | | Condition 2 | | Condition 3 | |
|---|---|---|---|---|---|---|
| | Release, g/inch (g/cm) | Re-adhesion, oz/inch (g/cm) | Release, g/inch (g/cm) | Re-adhesion, oz/inch (g/cm) | Release, g/inch (g/cm) | Re-adhesion, oz/inch (g/cm) |
| EX-15 | 9.9 (3.9) | 25.4 (284) | 10.3 (4.1) | 24.3 (271) | 17.6 (6.9) | 25.4 (284) |
| EX-16 | 9.5 (3.7) | 28.6 (319) | 8.9 (3.5) | 29.2 (326) | 16.9 (6.7) | 29.7 (332) |

What is claimed is:

1. An emulsion composition comprising:
   a) water;
   b) a polymerizable surfactant having an unsaturated group that can undergo free radical polymerization;
   c) a first monomer composition comprising
      1) an alkyl (meth)acrylate having an alkyl group with at least six carbon atoms;
      2) a first acidic monomer having a glass transition temperature equal to at least 100° C. when measured as a homopolymer; and
      3) a second acidic monomer having a glass transition temperature equal to no greater than 50° C. when measured as a homopolymer; and
   d) a second (meth)acrylate polymer in an amount of 0.5 to 15 weight percent based on a total weight of the first monomer composition, wherein
      the second (meth)acrylate polymer has a weight average molecular weight in a range of 3,000 to 150,000 Daltons,
      the second (meth)acrylate polymer has a glass transition temperature greater than −50° C., and
      the second (meth)acrylate polymer is formed from a second monomer composition comprising at least 10 weight percent of a non-acidic high $T_g$ monomer based on a total weight of monomers in the second monomer composition, the non-acidic high $T_g$ monomer having a glass transition temperature equal to at least 80° C. when measured as a homopolymer;
   wherein
      the emulsion has a first phase comprising water and a second phase dispersed as droplets within the first phase; and
      the droplets comprise a mixture comprising
         i) at least 85 weight percent of the first monomer composition; and
         ii) the second (meth)acrylate polymer, wherein the second (meth)acrylate polymer is not miscible with the first phase and wherein the second (meth)acrylate polymer is dissolved in the first monomer composition within the droplets.

2. The emulsion composition of claim 1, wherein the first monomer composition comprises:
   65 to 98.5 weight percent of the alkyl (meth)acrylate having at least six carbon atoms;
   0 to 20 weight percent of an alkyl (meth)acrylate having an alkyl group with one to five carbon atoms;
   0.5 to 5 weight percent of the first acidic monomer; and
   1 to 10 weight percent of the second acidic monomer,
wherein each amount is based on a total weight of monomers in the first monomer composition.

3. The emulsion of claim 1, wherein the first acidic monomer in the first monomer composition comprises acrylic acid, methacrylic acid, itaconic acid, maleic anhydride, maleic acid, or a mixture thereof and wherein the second acidic monomer in the first monomer composition comprises carboxyethyl acrylate, mono-2-acryloyloxyethyl succinate, or a mixture thereof.

4. The emulsion of claim 1, wherein the second (meth)acrylate polymer is a reaction product of a second monomer composition comprising:
   10 to 100 weight percent of the non-acidic high $T_g$ monomer;
   0 to 90 weight percent alkyl acrylate having a linear or branched alkyl group with at least four carbon atoms and/or an alkyl methacrylate having a linear or branched alkyl group with at least five carbon atoms;
   0 to 10 weight percent polar monomer that is an acid-containing monomer, a hydroxyl-containing monomer, or a mixture thereof,
wherein each amount is based on a total weight of monomers in the second monomer composition.

5. The emulsion composition of claim 1, wherein the non-acidic high $T_g$ monomer in the second monomer composition comprises an alkyl (meth)acrylate having a cyclic alkyl group with 6 to 12 carbon atoms.

6. The emulsion composition of claim 1, wherein the non-acidic high $T_g$ monomer in the second monomer composition comprises an alkyl methacrylate having a linear or branched alkyl group with 1 to 4 carbon atoms, acrylamide, (meth)acrylonitrile, N-alkyl acrylamide having an alkyl group with 1 to 10 carbon atoms, N,N-dialkyl acrylamide having alkyl groups with 1 to 10 carbon atoms, or a combination thereof.

7. The emulsion composition of claim 1, wherein the non-acidic high $T_g$ monomer comprises 1) a first high $T_g$ monomer comprising an alkyl (meth)acrylate having a cyclic alkyl group with 6 to 12 carbon atoms, an alkyl methacrylate having a linear or branched alkyl group with 1 to 4 carbon atoms, or a combination thereof, and 2) a second high $T_g$ monomer comprising acrylamide, (meth)acrylonitrile, N-alkyl acrylamide having an alkyl group with 1 to 10 carbon atoms, N,N-dialkyl acrylamide having alkyl groups with 1 to 10 carbon atoms, or a combination thereof.

8. The emulsion composition of claim 1, further comprising a C9-based hydrocarbon tackifier.

9. A latex composition comprising a polymerized product of the emulsion composition of claim 1, wherein the latex composition comprises polymeric latex particles.

10. The latex composition of claim 9 further comprising a tackifier that is water dispersible.

11. The latex composition of claim 9, wherein the polymeric latex particles have a single glass transition temperature as determined using a Differential Scanning calorimeter.

12. The latex composition of claim 9, wherein the second (meth)acrylate polymer and a polymerized product of the first monomer composition are together in the same polymeric particles.

13. A pressure-sensitive adhesive comprising a dried product of the latex composition of claim 9.

14. An article comprising:
   a) a substrate; and
   b) a first pressure-sensitive adhesive layer positioned adjacent to a first major surface of the substrate, wherein the first pressure-sensitive adhesive layer comprises the pressure-sensitive adhesive of claim 13.

15. A method of forming a pressure-sensitive adhesive, the method comprising:
   a) forming an emulsion composition according to claim 1,
   b) polymerizing the emulsion composition to form a latex composition comprising polymeric latex particles; and
   c) drying the latex composition to form the pressure-sensitive adhesive.

* * * * *

UNITED STATES PATENT AND TRADEMARK OFFICE
CERTIFICATE OF CORRECTION

| | |
|---|---|
| PATENT NO. | : 9,890,301 B2 |
| APPLICATION NO. | : 15/533536 |
| DATED | : February 13, 2018 |
| INVENTOR(S) | : Lili Qie et al. |

It is certified that error appears in the above-identified patent and that said Letters Patent is hereby corrected as shown below:

In the Specification

Column 6
Line 5, delete "North Rhime" and insert -- North Rhine --, therefor.
Line 9, delete "MAXENUL" and insert -- MAXEMUL --, therefor.

Column 11
Line 25, delete "-butylcylcohexyl" and insert -- -butylcyclohexyl --, therefor.

Column 14
Line 15, delete "pyrollidone" and insert -- pyrrolidone --, therefor.

Column 16
Line 29, delete "photoinitator" and insert -- photoinitiator --, therefor.

Column 19
Line 55, delete "trimehtylolpropane" and insert -- trimethylolpropane --, therefor.
Line 56, delete "tris(2-methyl-laziridine)" and insert -- tris(2-methyl-aziridine) --, therefor.
Line 57, delete "LCC" and insert -- LLC --, therefor.

Column 20
Line 62, delete "dicyclopenadiene," and insert -- dicyclopentadiene, --, therefor.

Column 23
Line 38, delete "tackifer" and insert -- tackifier --, therefor.
Line 57, delete "pentaertythritol" and insert -- pentaerythritol --, therefor.

Signed and Sealed this
Twenty-second Day of May, 2018

Andrei Iancu
*Director of the United States Patent and Trademark Office*

In the Claims

Column 47
Line 11, in Claim 15, delete "claim 1," and insert -- claim 1; --, therefor.